(12) United States Patent
Warren et al.

(10) Patent No.: US 8,821,851 B2
(45) Date of Patent: Sep. 2, 2014

(54) INFLAMMATION-INHIBITORY SERUM FACTORS AND USES THEREOF

(75) Inventors: H. Shaw Warren, Cambridge, MA (US); Jean-Marc Cavaillon, Chaville (FR)

(73) Assignees: The General Hospital Corporation, Boston, MA (US); Institut Pasteur, Paris (FR)

( * ) Notice: Subject to any disclaimer, the term of this patent is extended or adjusted under 35 U.S.C. 154(b) by 1146 days.

(21) Appl. No.: 12/225,496

(22) PCT Filed: Mar. 22, 2007

(86) PCT No.: PCT/US2007/007113
§ 371 (c)(1), (2), (4) Date: Sep. 23, 2008

(87) PCT Pub. No.: WO2007/111938
PCT Pub. Date: Oct. 4, 2007

(65) Prior Publication Data
US 2009/0175797 A1      Jul. 9, 2009

Related U.S. Application Data

(60) Provisional application No. 60/785,091, filed on Mar. 23, 2006.

(51) Int. Cl.
*A61K 38/00* (2006.01)
*A61P 31/00* (2006.01)
*A61P 29/00* (2006.01)

(52) U.S. Cl.
USPC ......... 424/85.2; 424/184.1; 514/2.1; 530/380

(58) Field of Classification Search
None
See application file for complete search history.

(56) References Cited

U.S. PATENT DOCUMENTS

| | | | |
|---|---|---|---|
| 7,285,633 B2 * | 10/2007 | Wu et al. ............... | 530/350 |
| 2001/0055630 A1 | 12/2001 | Castillo et al. | |
| 2003/0228583 A1 | 12/2003 | Amacher et al. | |
| 2003/0235577 A1 * | 12/2003 | Shapiro et al. ............ | 424/94.65 |
| 2004/0072261 A1 | 4/2004 | Kostanjevecki et al. | |
| 2005/0048574 A1 | 3/2005 | Kantor et al. | |
| 2005/0142569 A1 | 6/2005 | Guild et al. | |
| 2006/0014716 A1 | 1/2006 | Frey, II et al. | |

FOREIGN PATENT DOCUMENTS

| | | |
|---|---|---|
| WO | WO 2005/014622 A3 | 2/2005 |
| WO | WO 2005/014622 A2 | 1/2006 |
| WO | WO 2006/017573 A2 | 2/2006 |
| WO | WO 2006/021451 A2 | 3/2006 |

OTHER PUBLICATIONS

Liang et al. J Leuko Biol 86: 229-235, 2009.*
Wait et al (Proteomics 5: 4245-4253, 2005.*
Dekkers et al (Blood 94: 2252-2258, 1999).*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39,.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Lohrer et al. (Endocr 141: 4457-4465, 2000).*
NCBI page—GenBank Accession No. AAA58678.*
Altruda et al. J Mol Evol 27: 102-108, 1988—abstract.*
NCBI Accession # AAA58678.1 (protein sequence of human hemopexin), Dec. 31, 1994.*
International Preliminary Report on Patentability for International Application PCT/US2007/007113, dated Nov. 4, 2008.
International Search Report for International Application PCT/US2007/007113, mailed Oct. 7, 2008.
Written Opinion for International Application PCT/US2007/007113, mailed Oct. 7, 2008.
Camborieux et al., "Respective Roles of Inflammation and Axonal Breakdown in the Regulation of Peripheral Nerve Hemopexin: An Analysis in Rats and in C57BL/Wlds Mice," *J. Neuroimmunol.* 107(1): 29-41 (2000).
Das et al., "Structure and Evolutionary Aspects of Matrix Metalloproteinases: A Brief Overview," *Mol. Cell. Biochem.* 253(1-2): 31-40 (2003). (Abstract only).
European Search Report for European Patent Application No. 07753718.1, dated Apr. 28, 2011.
Fink, "Editorial: Hemopexin: Newest Member of the Anti-Inflammatory Mediator Club," *J. Leukoc. Biol.* 86(2): 203-204 (2009).
Heumann et al., "Role of Plasma, Lipopolysaccharide-Binding Protein, and CD14 in Response of Mouse Peritoneal Exudate Macrophages to Endotoxin," *Infect. Immun.* 69(1): 378-385 (2001).
Kapojos et al., "Regulation of Plasma Hemopexin Activity by Stimulated Endothelial or Mesangial Cells," *Nephron. Physiol.* 96(1): P1-P10 (2004). (Abstract only).
Larsen et al., "A Central Role for Free Heme in Pathogenesis of Severe Sepsis," *Sci. Trani. Med.* 2(51): 1-12 (2010).
Lin et al., "Synergistic Inflammation Is Induced by Blood Degradation Products with Microbial Toll-Like Receptor Agonists and Is Blocked by Hemopexin," *J. Infect. Dis.* 202(4): 624-632 (2010).
Novitsky et al., "Turbidimetric Method for Quantifying Serum Inhibition of *Limulus* Amoebocyte Lysate," *J. Clin. Microbiol.* 21(2): 211-216 (1985).
Piccard et al., "Hemopexin Domains as Multifunctional Liganding Modules in Matrix Metalloproteinases and Other Proteins," *J. Leukoc Biol.* 81(4): 870-892 (2007).
Saso et al., "Differential Changes in Alpha2-Macroglobulin and Hemopexin in Brain and Liver in Response to Acute Inflammation," *Biochemistry (Mosc).* 64(7): 839-844 (1999). (Abstract only).
Smith et al., "Role of Heme-Hemopexin in Human T-Lymphocyte Proliferation," *Exp. Cell Res.* 232(2): 246-254 (1997).

(Continued)

*Primary Examiner* — Daniel E Kolker
*Assistant Examiner* — Aditi Dutt
(74) *Attorney, Agent, or Firm* — Clark & Elbing LLP

(57) ABSTRACT

Disclosed are methods of purifying compounds that reduce or prevent an inflammatory response in a mammal, use of such compounds in treating a mammal having or being at risk of developing inflammation, as well as serum containing such purified compounds. Also disclosed are animal models that are more representative of humans in the study of inflammatory responses or as screening tools for discovering or developing new therapeutics or lead candidate compounds for inhibition of an inflammatory response.

11 Claims, 25 Drawing Sheets

(56) References Cited

OTHER PUBLICATIONS

Suzuki et al., "Inhibition of Mg2+-Dependent Adhesion of Polymorphonuclear Leukocytes by Serum Hemopexin: Differences in Divalent-Cation Dependency of Cell Adhesion in the Presence and Absence of Serum," *Cell Struct. Funct.* 28(4): 243-253 (2003).

Sukuki and Namiki, "[Serum Hemopexin: Suppressive Effect on Neutrophil Functions and Prospect of Clinical Application to Autoimmune Diseases]," *Nippon Rinsho* 62(3): 577-586 (2004). (Abstract only).

Tolosano and Altruda, "Hemopexin: Structure, Function, and Regulation," *DNA Cell Biol.* 21(4): 297-306 (2002).

Vranckx et al., "Inflammatory Competence of Fetal Rat: Acute-Phase Plasma Protein Response of the Fetus Treated by Turpentine in Utero," *Inflammation* 13(1): 79-90 (1989). (Abstract only).

Wagener et al., "Different Faces of the Heme-Heme Oxygenase System in Inflammation," *Pharmacol. Rev.* 55(3): 551-571 (2003).

Wait et al., "Reference Maps of Mouse Serum Acute-Phase Proteins: Changes with LPS-Induced Inflammation and Apolipoprotein A-I and A-II Transgenes," *Proteomics* 5(16): 4245-4253 (2005).

Warren, "Editorial: Mouse Models to Study Sepsis Syndrome in Humans," *J. Leukoc Biol.* 86(2): 199-201 (2009).

Watanabe et al., "Hemoglobin and its Scavenger Protein Haptoglobin Associate with ApoA-1-Containing Particles and Influence the Inflammatory Properties and Function of High Density Lipoprotein," *J. Biol. Chem.* 284(27): 18292-18301 (2009).

Yoneda et al., "Characterization of the Ligand Binding Activities of Vitronectin: Interaction of Vitronectin with Lipids and Identification of the Binding Domains for Various Ligands Using Recombinant Domains," *Biochemistry* 37(18): 6351-6360 (1998). (Abstract only).

Chen et al., "Increased Striatal Injury and Behavioral Deficits after Intracerebral Hemorrhage in Hemopexin Knockout Mice," *J. Neurosurg.* 114(4):1159-1167 (2011).

Eskew et al., "Cellular Protection Mechanisms Against Extracellular Heme. Heme-Hemopexin, but Not Free Heme, Activates the N-Terminal c-Jun Kinase," *J. Biol. Chem.* 274(2):638-648 (1999).

Fernandez et al., "Heme Amplifies the Innate Immune Response to Microbial Molecules through Spleen Tyrosine Kinase (Syk)-Dependent Reactive Oxygen Species Generation," *J. Biol. Chem.* 285(43):32844-32851 (2010).

Hunt et al., "Heme-Mediated Reactive Oxygen Species Toxicity to Retinal Pigment Epithelial Cells Is Reduced by Hemopexin," *J. Cell Physiol.* 168(1):81-86 (1996).

Hunt et al., "Hemopexin in the Human Retina: Protection of the Retina Against Heme-Mediated Toxicity," *J. Cell Physiol.* 168(1):71-80 (1996).

Larsen et al., "Supplementary Materials for: A Central Role for Free Heme in the Pathogenesis of Severe Sepsis," *Sci. Transl. Med.* 2(51): 51 ra71 (2010).

Mauk et al., "An Alternative View of the Proposed Alternative Activities of Hemopexin," *Protein Sci.* 20(5):791-805 (2011).

Mitchell et al., "Dual Stimulation of MyD88-Dependent Toll-Like Receptors Induces Synergistically Enhanced Production of Inflammatory Cytokines in Murine Bone Marrow-Derived Dendritic Cells," *J. Infect. Dis.* 202(2):318-329 (2010).

Monteiro et al., "Leukotriene $B_4$ Mediates Neutrophil Migration Induced by Heme," *J. Immunol.* 186(11):6562-6567 (2011).

Pong et al., "Association of Hemopexin in Tear Film and Conjunctival Macrophages with Vernal Keratoconjunctivitis," *Arch. Ophthalmol.* 129(4):453-461 (2011).

Suzuki et al., "Hemopexins Suppress Phorbol Ester-Induced Necrosis of Polymorphonuclear Leucocytes," *Cell Struct. Funct.* 26(4):235-241 (2001).

Wagener et al., "Herne-Induced Cell Adhesion in the Pathogenesis of Sickle-Cell Disease and Inflammation," *TRENDS Pharmacol. Sci.* 22(2):52-54 (2001).

Zhou et al., "Role of Extracellular Hemoglobin in Thrombosis and Vascular Occlusion in Patients with Sickle Cell Anemia," *Anemia* 2011, Article ID 918916: 1-5 (2011).

\* cited by examiner

INFLAMMATION-INHIBITORY SERUM FACTORS AND USES THEREOF

CROSS-REFERENCE TO RELATED APPLICATIONS

The present application is the U.S. National Stage of International Application No. PCT/US2007/007113, filed Mar. 22, 2007, which claims the benefit of U.S. Provisional Application Ser. No. 60/785,091, filed Mar. 23, 2006.

STATEMENT AS TO FEDERALLY FUNDED RESEARCH

The United States Government has a paid-up license in this invention and the right in limited circumstances to require the patent owner to license others on reasonable terms as provided for by the terms of Grant Numbers 5R01GM059694-06 and 5R01AI059010-02 awarded by the National Institutes of Health.

BACKGROUND OF THE INVENTION

The invention relates to methods of using serum factors having inflammation-inhibitory activity, for example, for reducing inflammation (e.g., autoimmune diseases such as rheumatoid arthritis and inflammatory bowel disease, and sepsis).

Autoimmune diseases are a serious problem. An estimated 2.1 million people in the United States are affected by rheumatoid arthritis, and an estimated one million are affected by inflammatory bowel disease. Additionally, severe sepsis (or septic shock) is one of the most important complications in non-coronary intensive care units. Despite new insights into the pathology of sepsis and the development of new antibiotics, the incidence of severe sepsis has increased in the last decades (Casey et al., *Ann. Intern. Med.* 119:771-778, 1993). The development of new treatment strategies has been disappointing, as is demonstrated by the continued high mortality (40-60%) (Casey et al., *Ann. Intern. Med.* 119:771-778, 1993; Balk et al., *Dis. Mon.* 50:168-213, 2004; Brun-Buisson et al., *J. Amer. Med. Assoc.* 274:968-974, 1995).

Thus there is a need for identification of factors that cause and/or inhibit inflammation responses, for example those caused by autoimmune diseases (e.g., rheumatoid arthritis and inflammatory bowel disease) and sepsis, and to identify methods of treatment for such diseases.

SUMMARY OF THE INVENTION

The present invention features methods of purifying compounds that reduce or prevent an inflammatory response in a mammal, use of such compounds in treating a mammal having or being at risk of developing inflammation, such as inflammation resulting from an increase in Tumor Necrosis Factor (TNF) expression or activity, as well as serum containing such purified compounds. The discovery of the compounds described herein also enables the development of animal models that are more representative of humans in the study of inflammatory responses or as screening tools for discovering or developing new therapeutics or lead candidate compounds for inhibition of an inflammatory response.

Accordingly, the first aspect of the invention features a method of purifying from serum a compound that reduces or prevents an inflammatory response in a mammal. This method involves (a) adding ammonium sulfate between 40% and 60% saturation to serum to separate the serum into a precipitate and a supernatant, (b) using chromatofocusing to separate the precipitate into fractions, (c) determining whether one of the fractions modulates a cytokine response in a cell, cell extract, or cell supernatant, and (d) isolating the compound contained in the fraction that alone or in combination with a second compound modulates the cytokine response, where the compound is a compound that reduces or prevents the inflammatory response in the mammal.

In a desirable embodiment of the first aspect of the invention, the serum is a mouse serum. In another desirable embodiment of the first aspect of the invention, step (d) involves use of a MonoQ high pressure liquid chromatography column, analytical sizing chromatography, or Sodium Dodecyl Sulfate gel electrophoresis.

In other desirable embodiments of the first aspect of the invention, the inflammatory response includes a modulation in the expression or activity of Tumor Necrosis Factor α, IL-6, IL-8, or IL-10. Desirably, the modulation is a decrease in the expression or activity of Tumor Necrosis Factor α, IL-6, or IL-8. In an additional desirable embodiment of the first aspect of the invention, the modulation is an increase in the expression or activity of IL-10.

In the second aspect, the invention features a method of reducing or preventing an inflammatory response resulting from a bacterial or viral infection or the presence of a bacterial toxin in a mammal. This method involves administering to the mammal a polypeptide containing a hemopexin amino acid sequence, in an amount sufficient to reduce or prevent the inflammatory response.

In the third aspect, the invention features another method of reducing or preventing an inflammatory response resulting from a bacterial or viral infection or the presence of a bacterial toxin in a mammal. This method involves administering to the mammal a transthyretin amino acid sequence, in an amount sufficient to reduce or prevent the inflammatory response.

In desirable embodiments of the second and third aspects of the invention, the inflammatory response results from the presence of a bacterial toxin. Desirably, the bacterial toxin is a component of a gram-negative bacterium and more desirably, the bacterial toxin is lipopolysaccharide.

In other desirable embodiments of the second and third aspects of the invention, the administering step decreases a cytokine response. Desirably, the cytokine response involves a decrease in Tumor Necrosis Factor α, IL-6, or IL-8 expression or activity. In additional desirable embodiments of the second and third aspects of the invention, the administering step increases a cytokine response. Desirably, the cytokine response involves an increase in IL-10 expression or activity.

In further desirable embodiments of the second and third aspects of the invention, the inflammatory response involves p38 MAP kinase, erk1/2, or NF-κB activation. Moreover, the mammal in the second and third aspects of the invention desirably is a human.

The fourth aspect of the invention features a method of reducing or preventing inflammatory bowel disease in a mammal. This method involves administering to the mammal a polypeptide containing a hemopexin amino acid sequence, in an amount sufficient to reduce or prevent the inflammatory bowel disease.

The fifth aspect of the invention features a method of reducing or preventing rheumatoid arthritis or inflammatory bowel disease in a mammal. This method involves administering to the mammal a polypeptide containing a transthyretin amino acid sequence, in an amount sufficient to reduce or prevent the rheumatoid arthritis or inflammatory bowel disease.

In a desirable embodiment of the fourth and fifth aspects of the invention, the mammal is a human.

The sixth aspect of the invention features a method of reducing or preventing an inflammatory response in a mammal. This method involves administering to the mammal a polypeptide containing a vanin-3, alpha-fetoprotein, or dermcidin amino acid sequence, in an amount sufficient to reduce or prevent the inflammatory response.

In desirable embodiments of the sixth aspect of the invention, the administering step decreases a cytokine response. Desirably, the cytokine response involves a decrease in Tumor Necrosis Factor α, IL-6, or IL-8 expression or activity.

In other desirable embodiments of the sixth aspect of the invention, the administering step increases a cytokine response. Desirably, the cytokine response involves an increase in IL-10 expression or activity.

In additional desirable embodiments of the sixth aspect of the invention, the inflammatory response involves p38 MAP kinase, erk1/2, or NF-κB activation.

In further desirable embodiments of the sixth aspect of the invention, the inflammatory response is an autoimmune disease. Desirably, the autoimmune disease is rheumatoid arthritis or inflammatory bowel disease.

In yet other desirable embodiments of the sixth aspect of the invention, the inflammatory response results in sepsis.

In another desirable embodiment of the sixth aspect of the invention, the inflammatory response is induced by a bacterial toxin. Desirably, the bacterial toxin is a component of a gram-negative bacterium and more desirably, the bacterial toxin is lipopolysaccharide.

Moreover, the mammal in the sixth aspect of the invention desirably is a human.

The seventh aspect of the invention features a method of identifying a candidate compound that reduces or prevents an inflammatory response in a non-human mammal. This method involves (i) contacting a non-human mammal having reduced expression in its serum of a polypeptide containing a hemopexin amino acid sequence with a candidate compound and a bacterial toxin and (ii) determining whether the candidate compound results in reduction or prevention of the inflammatory response relative to a control non-human mammal contacted with the candidate compound in the absence of the bacterial toxin.

The eighth aspect of the invention features another method of identifying a candidate compound that reduces or prevents an inflammatory response in a non-human mammal. This method involves (i) contacting a non-human mammal having reduced expression in its serum of a vanin-3, transthyretin, alpha-fetoprotein, or dermcidin amino acid sequence with a candidate compound and a bacterial toxin and (ii) determining whether the candidate compound results in reduction or prevention of the inflammatory response relative to a control non-human mammal contacted with the candidate compound in the absence of the bacterial toxin.

In desirable embodiments of the seventh and eighth aspects of the invention, the non-human mammal is a mouse, a rat, or a rabbit. Desirably, the non-human mammal is a mouse and more desirably, the mouse is a knock-out mouse.

In other desirable embodiments of the seventh and eighth aspects of the invention, the bacterial toxin is a component of a gram-negative bacterium. Desirably, the bacterial toxin is lipopolysaccharide.

The ninth aspect of the invention features a mammalian serum containing a purified hemopexin, vanin-3, transthyretin, alpha-fetoprotein, or dermcidin amino acid sequence. Desirably, the serum contains a purified polypeptide including a hemopexin amino acid sequence. In another desirable embodiment of the ninth aspect of the invention, the serum is human serum or fetal calf serum.

DEFINITIONS

By "polypeptide comprising a hemopexin amino acid sequence" as used herein is meant a polypeptide that is substantially identical to the amino acid sequence of GenBank Accession No. AAA58678 (*Homo sapiens*), NP_000604 (*Homo sapiens*), AAH19901 (*Mus musculus*), or NP_445770 (*Rattus norvegicus*), or a fragment thereof, or a polypeptide that contains a domain that is substantially identical to the amino acid sequence of AAA58678, NP_000604, AAH19901, or NP_445770, or a fragment thereof, and that can reduce or prevent an inflammatory response in a mammal. Desirably, a "polypeptide comprising a hemopexin amino acid sequence" is identical to the amino acid sequence of AAA58678 or NP_000604 or contains a domain that is identical to the amino acid sequence of AAA58678 or NP_000604. Assays for determining whether a "polypeptide comprising a hemopexin amino acid sequence" can reduce or prevent an inflammatory response in a mammal are described herein and include, for example, cell culture assays using, for example, monocytes.

By "vanin-3 amino acid sequence" as used herein is meant a polypeptide that is substantially identical to the amino acid sequence of GenBank Accession No. ABA60895 (*Homo sapiens*), CAC33872 (*Homo sapiens*), AAI11522 (*Mus musculus*), CAB59323 (*Mus musculus*), or XP_574282 (*Rattus norvegicus*), or a fragment thereof. Desirably, a "vanin-3 amino acid sequence" is identical to the amino acid sequence of ABA60895 or CAC33872 or contains a domain that is identical to the amino acid sequence of ABA60895 or CAC33872. Assays for determining whether a "vanin-3 amino acid sequence" can reduce or prevent an inflammatory response in a mammal are described herein and include, for example, cell culture assays using, for example, monocytes.

By "transthyretin amino acid sequence" as used herein is meant a polypeptide that is substantially identical to the amino acid sequence of GenBank Accession No. NP_000362 (*Homo sapiens*), NP_038725 (*Mus musculus*), or CAA70449 or NP_036813 (*Rattus norvegicus*), or a fragment thereof, and that can reduce or prevent an inflammatory response in a mammal. Desirably, a "transthyretin amino acid sequence" is identical to the amino acid sequence of NP_000362, NP_038725, or CAA70449 or NP_036813. Assays for determining whether a "transthyretin amino acid sequence" can reduce or prevent an inflammatory response in a mammal are described herein and include, for example, cell culture assays using, for example, monocytes.

By "dermcidin amino acid sequence" as used herein is meant a polypeptide that is substantially identical to the amino acid sequence of GenBank Accession No. NP_444513 (*Homo sapiens*), AAH69108 (*Homo sapiens*), AAL18349 (*Homo sapiens*), or AAN63881 (*Rattus norvegicus*), or a fragment thereof, or a polypeptide that contains a domain that is substantially identical to the amino acid sequence of NP_444513, AAH69108, AAL18349, or AAN63881, or a fragment thereof, and that can reduce or prevent an inflammatory response in a mammal. Desirably, a "dermcidin amino acid sequence" is identical to the amino acid sequence of NP_444513, AAH69108, or AAL18349 or contains a domain that is identical to the amino acid sequence of NP_444513, AAH69108, or AAL18349. Assays for determining whether a "dermcidin amino acid sequence" can reduce or prevent an inflammatory response in a mammal are described herein and include, for example, cell culture assays using, for example, monocytes.

By "alpha-fetoprotein amino acid sequence" as used herein is meant a polypeptide that is substantially identical to the amino acid sequence of GenBank Accession No. EAX05681 (*Homo sapiens*), AAH27881 (*Homo sapiens*), AAA37189 (*Mus musculus*), NP_031449 (*Mus musculus*), CAD86790 (*Mus musculus*), AAH66206 (*Mus musculus*), NP_036625 (*Rattus norvegicus*), CAA24567 (*Rattus norvegicus*), or AAH97344 (*Rattus norvegicus*) or a fragment thereof, and that can reduce or prevent an inflammatory response in a mammal. Desirably, an "alpha-fetoprotein amino acid sequence" is identical to the amino acid sequence of EAX05681, AAH27881, AAA37189, NP_031449, CAD86790, AAH66206, NP_036625, CAA24567, or AAH97344. Assays for determining whether an "alpha-fetoprotein amino acid sequence" can reduce or prevent an inflammatory response in a mammal are described herein and include, for example, cell culture assays using, for example, monocytes.

By "cytokine response" is meant an increase in expression or activity of a cytokine in a subject or in cell culture. Desirably, the cytokine response is induced by a bacterial component, such as lipopolysaccharide. In other desirable embodiments, the cytokine response involves induction or activation of Tumor Necrosis Factor α (TNFα), IL-6, IL-8, or IL-10. Desirably, a cytokine response also involves p38 MAP kinase, erk1/2, or NF-κB activation.

By, "inflammatory response" is meant the activation of the immune system in a subject. Desirably the subject is a mammal such as a human. An inflammatory response preferably involves the induction of cytokines and may result from an autoimmune disease such as rheumatoid arthritis or inflammatory bowel disease, or from contact of the mammal with a virus, a gram-negative bacterium, a gram-positive bacterium, or component thereof, such as lipopolysaccharide (LPS). Desirably the inflammatory response involves an agonist of a Toll-like receptor, for example, LPS.

By an "autoimmune disease" is meant an immune response against a self-antigen that results in inflammation or destruction of healthy tissue in a subject. Desirably the subject is a mammal, such as a human. Exemplary autoimmune diseases include rheumatoid arthritis, inflammatory bowel disease, type I diabetes, aplastic anemia, Graves' disease, systemic lupus erythematosus, celiac disease, multiple sclerosis, psoriasis, scleroderma, chronic inflammatory demyelinating polyneuropathy, pernicious anemia, polyarteritis nodosa, Sjogren's syndrome, premature ovarian failure, alopecia (baldness), polyglandular failure, hypothyroidism, polymyositis, Crohn's disease, ulcerative colitis, autoimmune hepatitis, hypopituitarism, myocarditis, Addison's disease, autoimmune skin diseases, uveititis, polymyalgia rheumatica, Goodpasture's syndrome, hypoparathyroidism, Hashimoto's thyoriditis, Raynaud's phenomenon, polymyaglia rheumatica, and Guillain-Barre syndrome. Desirably, an autoimmune disease is rheumatoid arthritis or inflammatory bowel disease.

By "purified" is meant separated from other components that naturally accompany it. Typically, a compound is substantially pure when it is at least 50%, by weight, free from proteins, antibodies, and naturally-occurring organic molecules with which it is naturally associated. Preferably, the compound is at least 75%, more preferably, at least 90%, and most preferably, at least 99%, by weight, pure. A substantially pure compound may be obtained by chemical synthesis, separation of the factor from natural sources, or production of the factor in a recombinant host cell that does not naturally produce the factor. Desirably, the compound is purified from serum. A compound, for example, a protein, may be purified by one skilled in the art using standard techniques, such as those described by Ausubel et al. (Current Protocols in Molecular Biology, John Wiley & Sons, New York, 2000). The compound is preferably at least 2, 5, or 10-times as pure as the starting material, as measured using polyacrylamide gel electrophoresis, column chromatography, optical density, HPLC analysis, or Western analysis (Ausubel et al. Current Protocols in Molecular Biology, John Wiley & Sons, New York, 2000). Preferred methods of purification include salt precipitation, gel filtration, hydrophobic interaction chromatography, ion exchange chromatography, lectin chromatography, reversed phase chromatography, chromatofocusing, as well as combinations of these methods.

By a compound that "modulates a cytokine response" is meant a compound that increases or decreases protein or nucleic acid level or activity of a cytokine in a cell, a cell extract, or a cell supernatant. For example, such a compound may increase or decrease RNA stability, transcription, translation, or protein degradation. It will be appreciated that the degree of modulation provided by a modulatory compound in a given assay will vary, but that one skilled in the art can determine the statistically significant change (e.g., a p-value≤0.05) in the level of the specific protein or nucleic acid affected by a modulatory compound. In desirable embodiments, the expression or activity of Tumor Necrosis Factor α, IL-6, IL-8, or IL-10 is modulated. In a more desirable embodiment, the expression or activity of Tumor Necrosis Factor α, IL-6, and/or IL-8 is reduced. In another desirable embodiment, the expression or activity of IL-10 is increased. In further desirable embodiments a compound that modulates a cytokine response activates p38 MAP kinase, erk1/2, or NF-κB.

By a "compound," "candidate compound," or "factor" is meant a chemical, be it naturally-occurring or artificially-derived. Compounds may include, for example, peptides, polypeptides, synthetic organic molecules, naturally-occurring organic molecules, nucleic acid molecules, and components or combinations thereof.

By a "protein" is meant two or more amino acids joined by a peptide bond. Proteins of the invention may exist as monomers, dimers, or other oligomers.

By a "bacterial toxin" is meant a compound produced by or part of a bacterium that results in an inflammatory response in a mammal. Desirably, the bacterial toxin is a component of a gram-negative bacterium. More desirably, the bacterial toxin is lipopolysaccharide (LPS).

By "substantially identical" is meant a polypeptide or nucleic acid sequence exhibiting at least 50%, preferably 60%, 70%, 75%, or 80%, more preferably 85%, 90% or 95%, and most preferably 99% identity to a reference amino acid or nucleic acid sequence. For polypeptides, the length of comparison sequences will generally be at least 15 contiguous amino acids, preferably at least 20 contiguous amino acids, more preferably at least 25, 50, 75, 90, 100, 150, 200, 250, or 300 contiguous amino acids, and most preferably the full-length amino acid sequence. For nucleic acids, the length of comparison sequences will generally be at least 45 contiguous nucleotides, preferably at least 60 contiguous nucleotides, more preferably at least 75, 150, 250, 300, 450, 600, 750, or 900 contiguous nucleotides, and most preferably the full-length nucleotide sequence.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

Substantially identical nucleic acid sequences also include nucleic acid sequences that hybridize to the complement of a given nucleic acid sequence under high stringency hybridization conditions. Exemplary high stringency hybridization conditions include hybridization at approximately 42° C. in about 50% formamide, 0.1 mg/ml sheared salmon sperm DNA, 1% SDS (Sodium Dodecyl Sulfate), 2×SSC (Sodium Citrate Buffer), 10% Dextran Sulfate, a first wash at approximately 65° C. in about 2×SSC, 1% SDS, followed by a second wash at approximately 65° C. in about 0.1×SSC. Alternatively, high stringency hybridization conditions may include hybridization at approximately 42° C. in about 50% formamide, 0.1 mg/ml sheared salmon sperm DNA, 0.5% SDS, 5×SSPE, 1×Denhardt's, followed by two washes at room temperature in 2×SSC, 0.1% SDS, and two washes at between 55-60° C. in 0.2×SSC, 0.1% SDS.

ADVANTAGES

The present invention provides a number of advantages. For example, mice are the classical and most frequently utilized animals for research in immunology and inflammation and rodents and baboons (another LPS-resistant animal) are often utilized to study the pathogenesis of sepsis, or for the study of potential drugs to treat sepsis. Data from these experiments are then extrapolated to make decisions regarding the benefits and risks of going forward with drug development or clinical trials at tremendous cost. In the overwhelming majority of these experiments, an assumption is made that the model has relevance for human disease. However, the use of rodents or baboons in the study of sepsis is complicated by a complete lack of understanding of why these species are so resistant to microbial toxins in comparison to man or other LPS-sensitive species. As described herein, the present invention provides compounds found in mice and, likely, other LPS-resistant mammals such as baboons, which are involved in the suppression of an inflammatory response. The identification of these compounds enables development of rodent or baboon models that are sensitive to LPS. For example, inactivation of the compound or compounds by the use of antibodies or knock-out animals generates models that are more sensitive to LPS. These animals better approximate human physiology than the current use of massive doses of LPS or the use of toxins such as actinomycin D or D-galactosamine to sensitize the animals.

Moreover, most cell culture experiments are performed in the presence of fetal calf serum. However, the effects of the serum are almost never taken into account when the results of such in vitro experiments are used as models for in vivo mechanisms. The presently disclosed invention clarifies the effect of serum on in vitro experiments and, therefore, is advantageous in the development of better in vitro models.

Identification of the compound(s) causing LPS resistance may allow development of therapeutics to treat inflammation, including septic shock response and inflammatory diseases such as inflammatory bowel disease and rheumatoid arthritis. The presently disclosed invention additionally provides methods for treatment of these diseases using the compound(s) of the invention.

Other features and advantages of the invention will be apparent from the following Detailed Description, the drawings, and the claims.

BRIEF DESCRIPTION OF THE DRAWINGS

FIG. 1A shows the effect of mouse or human sera on TNF production from human peripheral blood mononuclear cells (PBMCs) in the presence or absence of LPS. FIG. 1B shows dose response curves of LPS on PBMC in the presence of 5% or 10% of either human or mouse sera.

FIG. 3B has an expanded scale to show the mouse results.

FIG. 3D has an expanded scale to show the mouse results.

FIG. 16A shows a representative result of this experiment; FIGS. 16B and 16C show the mean of two experiments. Grey bars represent media alone, black bars represent cells stimulated with LPS.

DETAILED DESCRIPTION

Figure 1A:
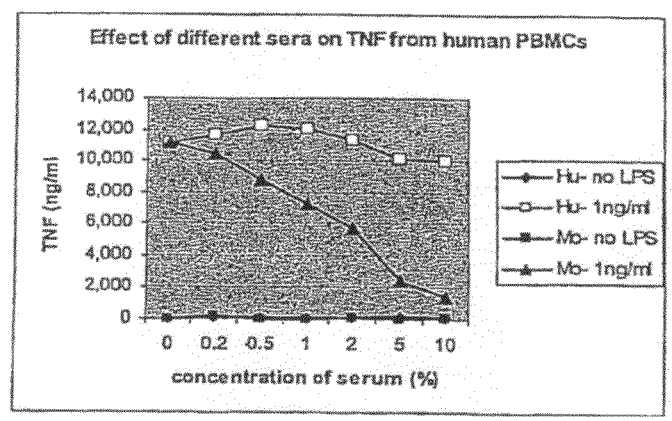
FIGS. 1A and 1B are graphs showing studies on the effects of human or mouse sera on LPS response.

The present invention is based on the discovery that serum factors are involved in the regulation of an inflammatory response. This discovery was made by comparing the response to LPS in the presence of serum from different species that exhibit differences in their LPS sensitivity. As a marker for the inflammatory response, cytokine expression, e.g., TNF or IL-6 levels, were measured in cell supernatants after stimulation with LPS. In addition, a correlation between in vitro cytokine production and in vivo LPS sensitivity, represented by the LD50 dose (mg/kg), was investigated for various species, and it was determined that serum factors played an important role in LPS sensitivity.

Tumor necrosis factor (TNF) (also known as cachectin) is one of the cytokines produced by macrophages in response to LPS (Beutler et al., *Nature* 320:584-588, 1986). TNF is believed to play a major role in the pathology of sepsis based upon three major findings. First, injection of recombinant TNF has been shown to produce septic shock symptoms in mice, rats, rabbits, dogs, sheep, humans, and calves (Johnson et al., *J. Appl. Physiol.* 66:1448-1454, 1989; Kenison et al., *Am. J. Vet. Res.* 52:1320-1326, 1991; Mathison et al., *J. Clin. Invest.* 81:1925-1937, 1988; Natanson et al., *J. Exp. Med.* 169:823-832, 1989; Remick et al., *Lab. Invest.* 56:583-590, 1987; Tracey et al., *Science* 234:470-474, 1986; Tracey et al., *Surg. Gynecol. Obstet.* 164:415-422, 1987). Second, pretreatment of mice or baboons with antibodies against TNF protects against the lethal effects of LPS (Beutler et al., *Science* 229:869-871, 1985; Tracey et al., *Nature* 330:662-664, 1987). Last, TNF knock-out mice showed prolonged survival after injection with LPS (Amiot et al., *Mol. Med.* 3:864-875, 1997).

A second cytokine produced by macrophages in response to LPS is IL-6 (previously called B-cell growth factor) (Brakenhoff et al., *J. Immunol.* 139:4116-4121, 1987). IL-6 is involved in producing an acute phase response (Suffredini et al., *J. Clin. Immunol.* 19:203-214, 1999). The pharmacokinetics of IL-6 are different from TNF; instead of a peak concentration after approximately one hour the IL-6 concentration rises more slowly but remains elevated for a longer period of time (van Deventer et al., *Blood* 76:2520-2526, 1990). Although infusion of IL-6 causes no adverse hemodynamic changes (Preiser et al., *Cytokine* 3:1-14, 1991), IL-6 has been shown to correlate best with mortality in septic patients (Waage et al., *J. Exp. Med.* 169:333-338, 1989; Hack et al., *Blood* 74:1704-1710, 1989) and is therefore considered as a marker for sepsis, rather than actually being involved in the pathology.

Of all sepsis cases, around 30-80% are caused by Gram-negative organisms (Glauser et al., *Pathogenesis. Lancet* 338: 732-736, 1991). Usually the innate immune response is sufficient to control infections. However, in sepsis, it is believed that the innate immune response is not able to control an infection and inflammation becomes generalized, possibly leading to harmful effects (Beutler, *Mol. Immunol.* 40:845-859, 2004). An important part of Gram-negative bacteria is endotoxin (also called lipopolysaccharide (LPS)). LPS is part of the outer membrane of Gram-negative bacteria (Beutler, *Mol. Immunol.* 40:845-859, 2004) and provokes an inflammatory response by signaling through Toll-like receptor 4 (TLR 4) (Poltorak et al., *Science* 282:2085-2088, 1998; Qureshi et al., *J. Exp. Med.* 189:615-625, 1999). TLR 4 is part of a family of Toll-like receptors which resembles Toll-receptors in *Drosophila* (Beutler, *Mol. Immunol.* 40:845-859, 2004; Janssens et al., *Clin. Microbiol. Rev.* 16:637-646, 2003; Medzhitov et al., *Nature* 388:394-397, 1997). TLR-4 is expressed in macrophages, dendritic cells, and endothelial cells, but not in lymphocytes (Janssens et al., *Clin. Microbiol. Rev.* 16:637-646, 2003). Considerable research has been done on LPS signaling and it is now believed that LPS first binds to CD14 (either a membrane bound form or a soluble form), which then transports LPS to the transmembrane signaling receptor TLR-4 (Guha et al., *Cell Signal* 13:85-94, 2001). The binding between LPS and CD14 is believed to be enhanced by LPS-Binding-Protein (LBP) (Schumann et al., *Science* 249: 1429-1431, 1990). TLR-4 needs to be associated with MD-2 before it can respond to LPS (Dziarski et al., *J. Endotoxin Res.* 6:401-405, 2000 and Shimazu et al., *J. Exp. Med.* 189:1777-1782, 1999. After LPS has bound to the complex of MD-2 and TLR-4, a complex signaling cascade starts, leading to translocating of Nuclear Factor-κB (NF-κB) from the cytosol to the nucleus of the cell (Beutler, *Mol. Immunol.* 40:845-859, 2004. This translocation results in transcription of many cytokines (Nathan, *Nature* 420:846-852, 2002).

Multiple experimental models, involving the use of various species, are currently used to study the pathogenesis of sepsis, but species differ widely in their sensitivity to LPS (Zweifach, *Fed. Proc.* 20:S18-S27, 1961; Redl et al., *Immunobiol.* 187: 330-345, 1993). At one end of the spectrum no harm can be detected in lizards after an injection of 200 mg/kg of LPS, where on the other end humans show severe symptoms of endotoxemia after an injection of only 0.02-0.04 µg LPS/kg (Clark, *Trans. R. Soc. Trop. Med. Hyg.* 76:4-7, 1982). Prior to the present invention, the reason for this profound difference in susceptibility to the harmful effect of LPS was unclear.

Mice and baboons are the most commonly used animal models to study human sepsis pathology. Both are much more resistant to LPS than humans. Although baboons show similar hemodynamic and hematologic changes after LPS injection, they require a $10^4$ fold higher dose than humans do to produce these symptoms (Haudek et al., *Shock* 20:431-436, 2003). Examples of other LPS-resistant animals include rats, chickens, lizards, and turtles (Zweifach, *Fed. Proc.* 20:S18-S27, 1961; Redl et al., *Immunobiol.* 187:330-345, 1993; Van Zee et al., *J. Immunol.* 146:3478-3482, 1991). On the other hand, examples of LPS-sensitive animals include humans, chimpanzees, rabbits, guinea pigs, cows, sheep, and horses.

In particular, the 50% lethal dose (LD50) for mice has been described to be around 15 mg LPS/kg (Reynolds et al., *J. Endotoxin Res.* 8:307-314, 2002), whereas severe shock is induced in humans after injection of 15 µg LPS/kg (Taveira et al., *N. Engl. J. Med.* 328:1457-1460 1993). This extreme difference in sensitivity to LPS is paralleled by cytokine production such as TNF and IL-6. Two nanograms/kg of LPS infused into humans reproducibly induce fever, TNF and IL-6 (van der Poll and Lowry, *Prog. Surg.* 20:18-32, 1995; Richardson et al., *Ann. Surg.* 210:239-245, 1989; van der Poll et al., *J. Infect. Dis.* 169:665-667, 1994). However, depending on the system, 100-50,000-fold this dose of LPS is needed to induce a similar cytokine response in rats or mice (Yamakawa et al., *Clin. Immunol. Immunopathol.* 79:256-262, 1996; Leon et al., *Am. J. Physiol.* 276:R81-R89, 1999).

Although this striking difference in sensitivity to LPS is well documented, the mechanisms underlying it were heretofore unknown. This relative insensitivity to LPS has resulted in the injection of comparatively large doses of LPS (micrograms or milligrams/kg) into rodent or baboon models in order to obtain a measurable response in their system. A different approach taken by some investigators has been to inject actinomycin D or D-galactosamine into mice at the same time as LPS. The sensitivity of mice to the lethal effects of LPS is increased by about 100,000-fold by concomitant administration of actinomycin D (Pieroni et al., *Proc. Soc. Exp. Biol. Med.* 133:790-794, 1970) or D-galactosamine (Galanos et al., *Proc. Natl. Acad. Sci. USA* 76:5939-5943, 1979) which makes mice 100-fold more sensitive to LPS. Toxicity due to inhibition of protein synthesis and induction of liver failure (Nowak et al., *Am. J. Physiol. Regul. Integr. Comp. Physiol.* 278:R1202-R1209, 2000) of these and other similar chemicals limits their use as reliable research models for sepsis.

Interestingly the clear resistance of mice to LPS seen in vivo is not reflected by in vitro experiments using fetal calf serum (FCS). Mouse macrophages cultured in vitro in FCS produce cytokines after stimulation with approximately 1 ng LPS/ml. Human macrophages cultured in FCS have the same threshold for cytokine production in vitro. Both produce roughly the same amount of TNF after stimulation with LPS. There are small variations in the sensitivity of mouse cells from different tissue locations, and there are scattered reports that the cellular response of murine and human cells can distinguish between subtle variations in the fatty acids of the lipid A of some organisms, such as strains of *P. aeruginosa* from patients with cystic fibrosis (Hajar et al., *Nat. Immunol.* 3:354-359, 2002). Nevertheless, most cells of the monocyte macrophage lineage in both species produce TNF in response to 1-10 ng/ml LPS derived from most enteric Gram-negative bacteria (Hajjar et al., *Nat. Immunol.* 3:354-359, 2002; Perera et al., *J. Immunol.* 158:4422-4429, 1997; Cavaillon et al., *Infect. Immunol.* 58:2325-2382, 1990; Warren et al., *J. Exp. Med.* 177:89-97, 1993). Therefore, defects or genetic polymorphisms in the macrophage cell line of mice, either in receptors such as the TLRs (Smirnova et al., *Genome Biol.* 1, 2000), or anywhere in the downstream signaling pathway, are unlikely to explain the difference in resistance to LPS that is seen in vivo between mice and humans.

The following examples are meant to illustrate the invention and should not be construed as limiting.

EXAMPLE 1

Mice and Humans Exhibit Different Sensitivities to LPS

Very little TNF or IL-6 is made in the whole blood of mice as compared to in human whole blood after ex vivo stimulation with LPS. Mouse and human sera neutralize LPS equally as assessed by the *Limulus* Amoebocyte Lysate assay, and mouse serum and decomplemented mouse serum markedly suppresses LPS-induced cytokines from human monocytes. Sera from LPS-resistant species (e.g., mouse, baboon, and chicken) but not sera from LPS-sensitive species (e.g., human, fetal calf) suppress production of TNFα from mouse macrophages. The suppression of macrophages is not limited to LPS, but extends to many PAMPs. Mouse and baboon serum facilitate mouse macrophages to produce IL-10. Serum from LBP KO and CD14 KO mice also suppress induction of TNF from monocytes. Mouse serum inhibits IL-6 and IL-8 production from human umbilical vein endothelial cells. The suppression of cytokines induced by mouse serum is not due to cellular toxicity. Exposure of mouse serum to trypsin on beads removes suppressive activity. Pre-exposure of human peripheral mononuclear cells to media containing mouse serum downregulates the cells.

The in vitro sensitivity of different human and mouse macrophage populations and endothelial cells to LPS in the presence of mouse, human, or fetal calf sera can be assessed by assaying cytokine production and/or adhesion molecule expression. Mouse cells that are useful for such assays include peritoneal macrophages, bone marrow derived macrophages, alveolar macrophages, peripheral blood mononuclear cells, endothelial lung cells, and the RAW 264.7 cell line. Human cells include peripheral blood mononuclear cells, the human THP-1 cell line, umbilical vein endothelial cells, and lung endothelial cells. The effects of sera from multiple LPS-sensitive species (e.g., human, chimpanzee, cow, horse, pig, hamster, guinea pig, or rabbit) with sera from LPS-resistant species (e.g., mouse, rat, baboon, chicken, or lizard) on the production of cytokines from mouse and human monocytes/macrophages can also be compared. PAMPs (pathogen-associated molecular pattern molecules) (e.g., heat killed Gram-negative and Gram-positive bacteria, bacterial lipoproteins, synthetic TLR2 agonists, LPS, flagellin peptidoglycans, and CpG DNA) may be used to study the effects of multiple different microbial stimuli that activate cells through Toll-like receptors on murine and human macrophages in the presence of mouse, human, and fetal calf sera. Further, multiplex bead technology and/or ELISA may be used to study the effects of mouse, human, and fetal calf serum on the production of an extensive panel of different LPS-induced cytokines from human and mouse monocytes/macrophages.

Comparing the Effects of Mouse and Human Serum on Different Cultured Cells

Immune and endothelial cells are critically involved in inflammation response (e.g., inflammatory disease and severe sepsis). A thorough understanding of the interaction of these cells with microbial products can facilitate the understanding of basic mechanisms of inflammation. The suppression (or the facilitation) of sera of different species on macrophages and endothelial cells of human and mouse origin with different stimuli using readouts pertinent to the cell type can be compared systematically.

Effects of Sera on Macrophage Cells

The effects of fetal calf serum, mouse serum, and human serum on macrophages and endothelial cells can be compared. Studies of bacterial diseases and sepsis have used a variety of different cell types for in vitro assays. For most experiments LPS, the synthetic peptide Pam3cys, and killed whole *E. coli* bacteria are used to provide stimulation through TLR4 (LPS), TLR2 (Pam3Cys), and through multiple simultaneous receptors (killed *E. coli*).

Induced peritoneal macrophages, bone marrow derived macrophages, mouse alveolar macrophages, the RAW264-7 macrophage-like cell line, and mouse peripheral blood mononuclear cells (purified from pooled mouse blood) may be used for the assays described herein and in Bannerman, R. M., *Hematology. The mouse in biomedical research* (Academic Press, Inc., 1983: 293-312). Human cells suitable for the assays described herein include HPBMCs and ThP-1 cells. Each type of mononuclear cells in blood may be purified using means suitable that particular cell type. In particular, purified total mononuclear cells, as well as an enriched monocyte/macrophage population may be compared from each species by positive or negative selection. These cells can then be counted and stimulated in non-adherent and adherent conditions (Petit-Bertron et al., *J. Leukoc. Biol.* 73:145-154, 2003).

Cytokines produced by each type of macrophage can be suppressed by exposing the cells to the mouse sera, irrespective of the initial tissue source. Because of the variety of leukocyte cell types in mouse blood, comparing isolated mouse peripheral blood cells to human cells requires careful interpretation of the results. Adherent monocytes as well as non-adherent purified cell populations may also be compared using negative selection techniques, again with careful interpretation of results.

Effects of Sera on Endothelial Cells

Endothelial cell expression of adhesion molecules, such as P-selectin and E-selectin, and chemokines, such as IL-8, are crucial for migration of inflammatory cells to areas of inflammation and infection (Frenette and Wagner, *N. Engl. J. Med.* 335:43-45, 1996). The suppression of pro-inflammatory activation of endothelial cells by mouse serum can be evaluated.

Mouse serum may decrease all pro-inflammatory readouts in the endothelial cells that are induced by agonists of a Toll-like receptor, such as LPS, Pam3Cys, and killed *E. coli*. These experiments can also confirm that the modulation by mouse serum on human and mouse macrophages is independent of the macrophage signaling receptor that mediates the response. This information may be important to understand the breadth of the suppression. Thus, the mouse serum may suppress the cytokine response from both mouse and human endothelial cells induced by all of the PAMPs.

To assay an inflammatory response, cell-based ELISA is preferred, as it offers the advantages of being able to efficiently study many different conditions in one experiment without having to treat adherent cells with trypsin prior to analysis, if the sensitivity and specificity of this method is adequate for these studies. However use of other techniques, such as FACS analysis as described in Ruan et al. (*J. Vasc. Res.* 38:13-19, 2001), and multiplex bead technology may be desirable.

As PAMPs from commercial sources are often contaminated with trace amounts of other microbial products (Hellman et al., *J. Infect. Dis.* 188:286-289, 2003), caution is required in interpreting what is in each TLR agonist. However, it is unlikely that trace contamination in PAMPs can greatly alter the interpretation of results.

Endothelial cells are devoid of CD14 on their cell surface, and are therefore dependent upon soluble CD14 (sCD14) for signaling by LPS. Mouse serum contains 0.25 µg/ml sCD14 (Merlin et al., *Eur. J. Immunol.* 32:761-772, 2002), which is 100-fold the minimal amount of sCD14 that is sufficient to permit activation of macrophages from CD14 KO mice (2.5 ng/ml) (Haziot et al., *Immunity* 4:407-414, 1996). Nevertheless, it may be desirable to supplement the final concentration of mouse serum with 2 µg/ml recombinant sCD14 (Biometec, Greifswald, Germany) to avoid any confusion in interpretation.

The Response of Human Peripheral Blood Mononuclear Cells (PBMCs) to LPS is Markedly Decreased in the Presence of Mouse, but not Human Serum The effect of mouse versus human serum on the production of TNF by human adherent PBMCs was assayed as follows. PBMCs were isolated from the blood of human volunteers as described (Petit-Bertron et al., *J. Leukoc. Biol.* 73:145-154, 2003), adjusted for cell density, and studied in the presence of a fixed concentration of 1 ng/ml LPS and in media containing varied concentrations of mouse or human serum (FIG. 1A). There was a strong dose-dependent suppression of TNFα in the presence of mouse serum, occurring at less than 1% mouse serum, but not in human serum.

Figure 1B:
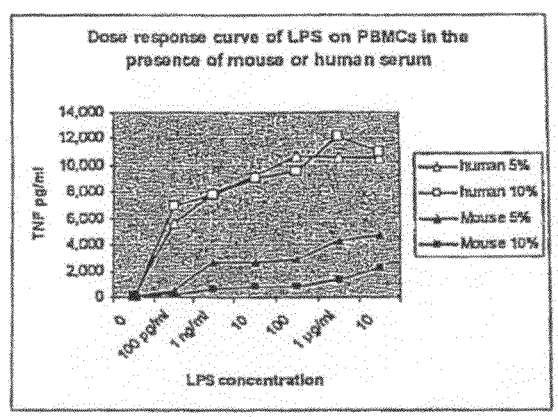

This experiment was repeated using 5% and 10% of mouse and human serum, and varied concentrations of LPS (FIG. 1B). The same levels of TNF attained with human serum were not attained with either concentration of mouse serum, and 100,000-fold more LPS (10 µg/ml) in mouse serum was required to achieve similar levels of TNF as stimulation with 100 pg/ml LPS in human serum. All of these experiments have been repeated at least three times.

Figure 2A:
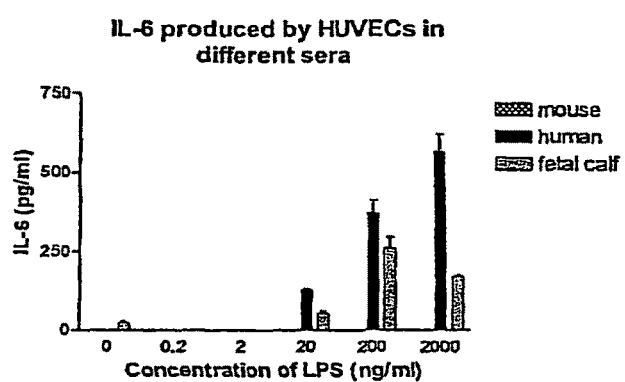
FIGS. 2A and 2B are graphs showing IL-6 (FIG. 2A) and IL-8 (FIG. 2B) produced by human umbilical vein endothelial cells (HUVEC) in mouse, human, and fetal calf serum over LPS concentrations ranging from 0.2 ng/ml to 2000 ng/ml.
Figure 2B:
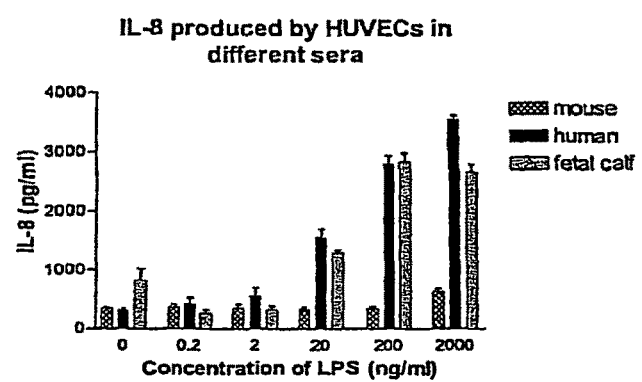

LPS Activates Human Endothelial Cells in the Presence of Human and Fetal Calf, but not Mouse Serum To determine if different types of serum affect whether LPS activates human endothelial cells in culture, the following assays were performed. Cryopreserved cultures of human umbilical vein endothelial cells (HUVEC, passage 3) were thawed and incubated at 37° C. under humidified 5% $CO_2$ in endothelial cell basal medium supplemented with epidermal growth factor, fibroblast growth factor, vascular endothelial growth factor, vitamin C, recombinant insulin-like growth factor, gentamicin, amphotericin, heparin, and 2% fetal calf serum. When cultures reached 80% confluence, cells were detached by brief exposure to trypsin/EDTA and then neutralized with trypsin neutralizing solution. Cells were pelleted, suspended in medium, placed in 96-well plates (20,000 cells/well), incubated overnight, washed, and incubated for 18 hours with dilutions of LPS in media containing either mouse, human, or fetal calf serum. Cell supernatants were evaluated for the presence of IL-6 and IL-8 by ELISA. LPS activated the cells in the presence of human and fetal calf serum, but not mouse serum (FIGS. 2A and 2B). This experiment has been repeated twice with similar results.

Endothelial cells lack CD14 on their surface; their activation by LPS is dependant upon soluble CD14 (sCD14) in the serum. To test if these cells do not respond due to insufficient sCD14 in the mouse serum (0.25 µg/ml) relative to the other two species (Merlin et al., *Eur. J. Immunol.* 32:761-772, 2002). The activation of HUVECs in the presence of human serum, or in the presence of recombinant mouse CD14 (Biometec, Greifswald, Germany) as a source of exogenous CD14 were studied HUVECs were prepared as above. The cells were then washed and incubated with LPS in media containing 1% human serum or 1 µg/ml CD14 together with additional mouse, human or fetal calf serum at concentrations of 5%. Supernatants were collected at 18 hours and tested as above. These results were essentially the same as shown above, and indicate that mouse serum contains a substance that inhibits LPS activation of endothelial cells, even in the presence of 1% human serum or exogenous sCD14.

Figure 3A:
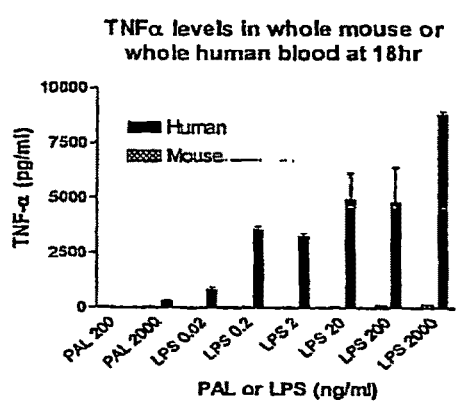
FIGS. 3A and 3B are graphs showing TNFα levels in whole mouse blood or whole human blood after 18 hours at various concentrations of peptidoglycan-associated lipoprotein (PAL) or LPS.
Figure 3B:
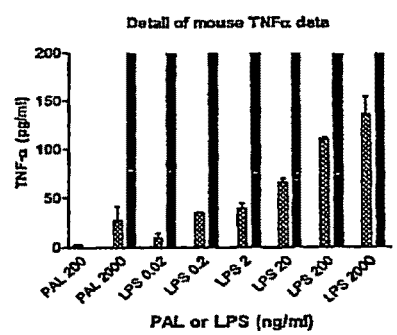
Figure 3C:
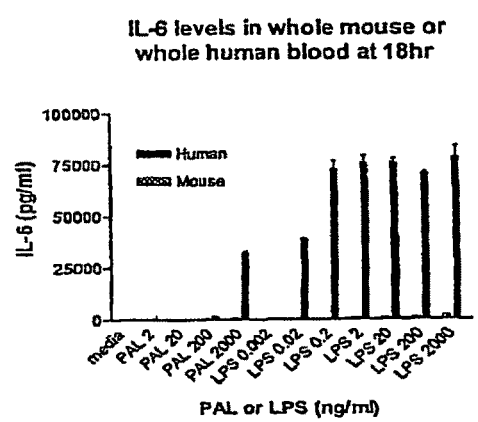
FIGS. 3C and 3D are graphs showing IL-6 levels in whole mouse or whole human blood after 18 hours at various concentrations of PAL or LPS.
Figure 3D:
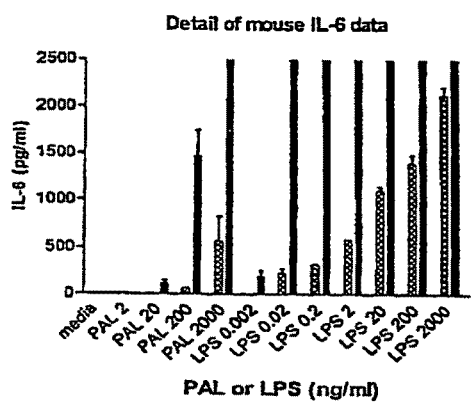

Very Little TNF or IL-6 is Made in the Whole Blood of Mice after Ex-Vivo Stimulation with LPS The LPS-induced cytokine response of mice and humans were further characterized using an ex-vivo whole blood assay (Wilson et al., *J. Immunol. Meth.* 139:233-240, 1991). Blood was drawn from mice or human volunteers into heparin, diluted 1:4 in RPMI media, stimulated with dilutions of *E. coli* O111:B4 LPS (ultrapure, Sigma) and analyzed at 18 hours for TNF and IL-6 by ELISA (FIGS. 3A and 3C), essentially as described by Warren et al. (*J. Esp. Med.* 177:89-97, 1993) and Wilson et al. (*J. Immunol. Meth.* 139:233-240, 1991). FIGS. 3B and 3D have expanded scales to show the mouse data.

Remarkably, even at high concentrations of LPS (2000 ng/ml), only a minimal amount of each cytokine is produced in mouse whole blood compared to in human whole blood. The cytokine response to peptidoglycan-associated lipoprotein (PAL), a Gram-negative bacterial membrane protein that stimulates cytokine production from macrophages in nanogram concentrations (Hellman et al., *J. Biol. Chem.* 277: 14274-14280, 2002) has a similar effect as LPS. Mouse (Haziot et al., *Immunity* 4:407-414, 1996) and human (Warren et al., *J. Exp. Med.* 177:89-97, 1993) peripheral blood monocytes are sensitive to 1 ng/ml LPS in fetal calf serum. The breadth of the suppression of macrophages by other PAMPs is addressed below. These experiments have been repeated six times with the same result using different mouse and human donors.

Mouse (and Baboon) Serum Induces Increased Production of IL-10 from Mouse and Human Macrophages while Decreasing TNFα

Figure 4A:
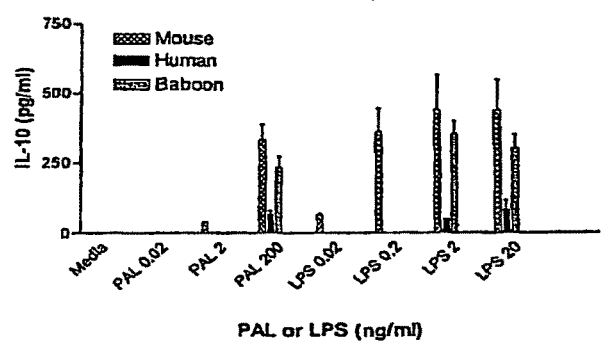
FIGS. 4A and 4B are graphs showing production of IL-10 (FIG. 4A) or TNFα (FIG. 4B) from mouse peritoneal macrophages in the presence of 10% serum from mouse, human, or baboon at several concentrations of PAL and LPS.
Figure 4B:
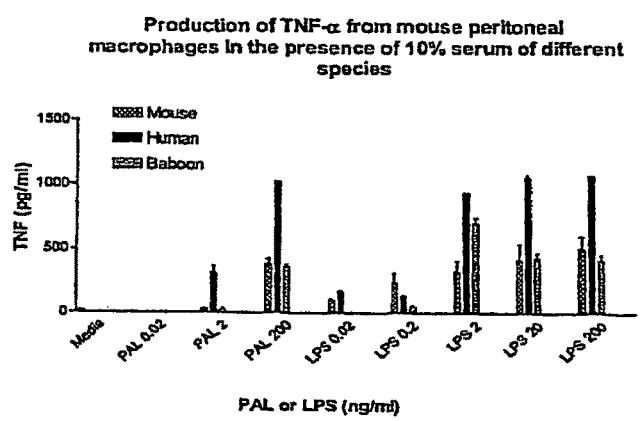

The production of LPS-induced IL-10, an anti-inflammatory cytokine, from mouse peritoneal macrophages and PBMCs was compared in the presence of human or mouse serum. These experiments, shown in FIGS. 4A and 4B for mouse macrophages, indicate that while mouse serum suppresses TNF, it facilitates IL-10 from both mouse and human macrophages. The same results are generated when human peripheral blood monocytes were studied. These studies were also compared using baboon serum, an LPS-resistant animal, and similar results were observed as with mouse serum. These experiments have been repeated twice due to limited supply of baboon serum. The facilitation of IL-10 and suppression of TNF by mouse serum compared to human serum have been repeated four times with mouse peritoneal macrophages, twice with mouse bone marrow derived macrophages, and four times with human PBMCs.

Figure 5:
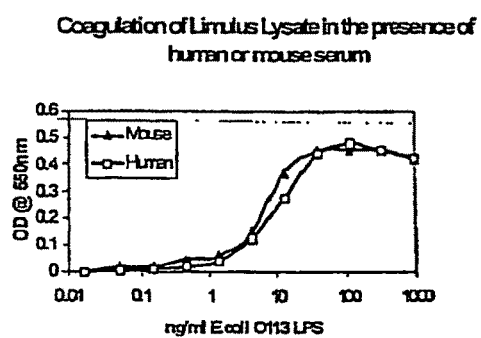
FIG. 5 is a graph showing coagulation of *Limulus* Amoebocyte Lysate in the presence of human or mouse sera at varying concentrations of LPS. No significant differences between the sera are observed.

The Response of *Limulus* Amoebocyte Lysate to LPS is the Same in the Presence of Mouse and Human Serum The bioactivity of LPS in mouse and human serum was also compared using the activation of *Limulus* Amoebocyte Lysate (LAL). This assay measures the neutralization of LPS by sera (Novitsky et al., *J. Clin. Micro.* 20:211-216, 1985). Dilutions of LPS were incubated in the sera of each species at a final dilution of 1:4 in the presence of a spectrophotometric lot of LAL in a microdilution plate. After one hour, coagulation of the LAL was assessed by optical density at 550 nm and plotted. The coagulation of LAL was identical in the presence of the two sera (FIG. 5). Thus, the difference in the whole blood assays shown above is likely not due to binding and neutralization of the bioactive lipid A moiety of LPS by a substance in mouse serum, at least as detected by *Limulus* Amoebocyte Lysate. This experiment was repeated three times.

Mouse Serum is not Toxic for Human Peripheral Blood Mononuclear Cells

To confirm that mouse serum is not toxic to human cells, the following experiments were performed. Adherent human PBMCs were incubated with 5% mouse (Balb/c) or human serum overnight, and the cellular viability was assessed by the tetrazolium salt assay (MTT test) (Hansen et al., *J. Immunol. Methods* 119:203-210, 1989). These results, reported as the mean of quadruplicates in a single experiment in Table 1, indicate that there is no significant toxicity to the cells caused by the mouse serum.

TABLE 1

Absence of toxicity as determined by MTT

| | 5% human | 5% mouse |
|---|---|---|
| No LPS, Mean (SEM) | 0.697 (0.028) | 0.702 (0.028) |
| LPS 10 ng/ml, Mean (SEM) | 0.754 (0.003) | 0.847 (0.012) |

These results likely reflect suppression by mouse sera on the cells rather than a toxic effect of mouse (or baboon) serum on the cells. First, mouse sera inhibits TNF production from mouse cells as well as human cells (see below); it is not expected for mouse serum to be toxic to mouse cells. Second, these same cells make IL-10 which would not be expected if toxicity was present. Third, as shown in the table above, no cellular toxicity is caused by the mouse serum as measured using the vital dye, MTT.

Complement is not Required for the Inhibition of TNF from Human Cells by Mouse Serum The fetal calf serum used in most laboratories as a supplement to tissue culture media is de-complemented. To exclude effects of complement in the mouse and human serum, and to gain insight into the stability of the factor, both sera were heated at 56° C. to de-complement the sera prior to testing. This had no effect on the suppressive effect of mouse sera on the production of TNF (data not shown). This experiment was repeated twice.

Mouse Serum Suppresses TNF from Numerous Stimuli, Including Numerous Pathogen-Associated Pattern Molecules To further characterize the effect of mouse serum on the induction of TNF, production of TNF from human peripheral blood monocytes was compared using multiple stimuli in the presence of either mouse or human serum. These results (Table 2) indicate that the active compound(s) in mouse serum markedly suppresses TNF production induced by numerous pro-inflammatory stimuli that are mediated by different Toll-like receptors. This experiment was repeated twice.

TABLE 2

Percent change in cytokine production by human peripheral blood monocytes in the presence of 10% mouse serum as compared to 10% human serum

| | TNF | | released IL-1β | | Intracellular IL-1α | |
|---|---|---|---|---|---|---|
| Stimulus | exp. I | exp. II | exp. I | exp. II | exp. I | exp. II |
| *E. coli* LPS 1 ng/ml | −93 | −98 | −84 | −88 | −58 | −55 |
| Peptidoglycan 10 µg/ml | −98 | −87 | −84 | −57 | −46 | −13 |

TABLE 2-continued

Percent change in cytokine production by human peripheral blood monocytes in the presence of 10% mouse serum as compared to 10% human serum

| Stimulus | TNF | | released IL-1β | | Intracellular IL-1α | |
|---|---|---|---|---|---|---|
| | exp. I | exp. II | exp. I | exp. II | exp. I | exp. II |
| Zymosan 100 µg/ml | −97 | −95 | −67 | −32 | −17 | −17 |
| TSST-1 10 µg/ml | −97 | −81 | nd | −77 | −53 | −34 |
| CpG 6 µg/ml | −88 | −85 | nd | −67 | −99 | −96 |
| PAL 4 µg/ml | −83 | −74 | −100 | −53 | −28 | −64 |

Figure 6:
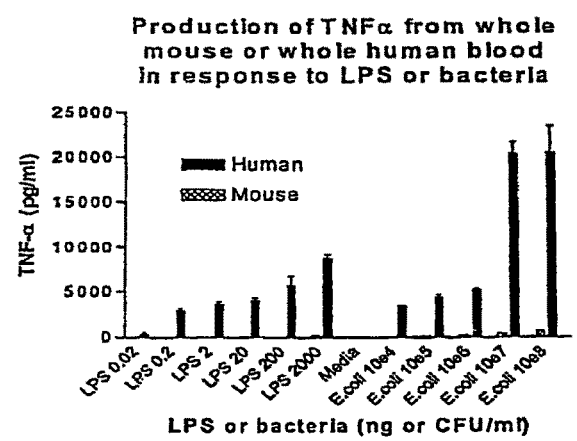
FIG. 6 is a graph showing production of TNFα from whole mouse or whole human blood in response to LPS or bacteria.

Experiments using the same design as described above but using whole heat killed *E. coli* O18K+ bacteria as a stimulus for the whole blood assay were also performed (Prins et al., *Infect. Immunol.* 63:2236-2242, 1995) (FIG. 6). The bacterial stimulation experiments were done twice, indicating that even very large concentrations of killed whole bacteria are unable to induce TNF in mouse blood using a well established assay. A parallel observation holds for IL-6. Very small amounts of TNF are made in comparison with the results in human whole blood. This large difference in response parallels the in vivo response of the two species.

Sera from LBP KO and CD14 KO Mice also Suppress Induction of TNF from Monocytes

Figure 7:
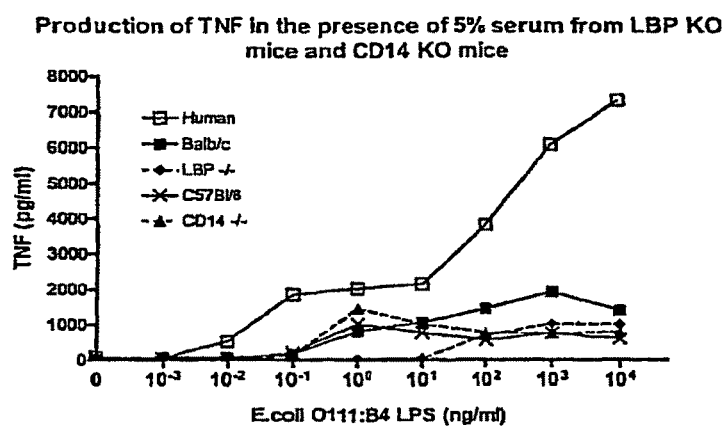
FIG. 7 is a graph showing production of TNF in the presence of 5% serum from human, Balb/c mice, C57Bl/6 mice, LPS binding protein (LBP) KO mice, and CD14 KO mice over a range of concentrations of *E. coli* O111:B4 LPS.

As LBP and CD14 are known to interact with and modulate the effects of LPS, it was assessed whether either plays a role in the downregulation of LPS-induced TNF from monocytes by mouse serum. Sera were obtained at the Pasteur Institute (Paris, France) from LBP KO (knock-out) mice (LBP−/−) or their background control mice (Balb/c) and CD14 KO mice (CD14−/−) or their background control mice (C57Bl/6). The effect of each serum on LPS-induced TNF production from human peripheral blood monocytes was evaluated (FIG. 7). Serum deficient in CD14 was equally efficient in suppressing TNF as the background control. Both the LBP-deficient serum and the control serum suppressed TNF relative to the human serum control. Slightly less TNF was induced in the presence of LBP-deficient serum as compared to the background control mouse serum. These experiments, performed twice, suggest than neither CD14 nor LBP is the mouse factor that downregulates the monocytes. Although both LBP KO serum and wild-type serum suppressed TNF, the slight further depression of TNF production in LBP deficient serum may be due to slightly less efficient LPS-induced TLR4 signaling in the absence of LBP.

Pre-Exposure of Human Peripheral Mononuclear Cells to Media Containing Mouse Serum Downregulates the Cells To determine whether direct contact between a compound in mouse serum and LPS is necessary for suppression of a cytokine response, human peripheral blood mononuclear cells or mouse bone marrow macrophages were washed and exposed to RPMI containing 5% mouse serum, 5% human serum, or no serum for 3 hours, at which point the media was replaced with RPMI without serum for all of the samples. The cells were then cultured in the presence of LPS (1 ng/ml) or Pam3Cys (10 µg/ml) for 24 hours, after which cytokines were measured in the supernatants. Macrophages that had been pre-incubated with media containing mouse serum (but not macrophages that had been pre-incubated in media containing human or fetal calf serum) were suppressed in a similar manner as parallel experiments in which the cells were stimulated in the presence of the serum containing media. These results indicate that direct physical contact between the mouse serum protein and the stimulant is not necessary for the suppression and that the three-hour exposure of the cells to the mouse protein downregulates the cytokine response of the cells. This experiment has been repeated twice with human PBMCs, and twice with mouse bone marrow macrophages with similar results (data not shown).

Determination of Cytokine Suppression and Facilitation from Mouse and Human Macrophages by Mouse, Human, and Fetal Calf Serum To assay the breadth of the modulation of different cytokines by mouse and human macrophages in the presence of mouse serum, the response of mouse peritoneal macrophages and human PBMCs to LPS in the presence of no serum or 5% fetal calf, mouse, and human serum may be compared.

There may be a variable response depending upon the cytokine. Some cytokines can be suppressed by mouse serum (e.g., TNF and IL-6) and other cytokines can be facilitated (e.g., IL-10). No prior systematic efforts to identify the cause of differences between sera of different species (e.g., differences between mouse and human sera) have previously been undertaken. Which mediators are facilitated and which are suppressed when mouse cells are stimulated in the presence of mouse serum can be determined.

As above conventional ELISA is preferred. Multiplexed bead technologies can also be used; the system and kit that is best validated by testing is chosen. In one example, ELISAs may be performed for a selected group of the cytokines that are of main interest along with the use of multiplexed bead technologies for other cytokines.

LPS Response is Mediated by a Compound(s) in Serum

The above experiments indicate that the differential effect of mouse and human serum is likely due to serum factors. In particular, LPS has similar activity after pre-incubation in mouse and human serum, as tested by the coagulation of the cell free coagulation cascade in *Limulus* Amoebocyte Lysate (Novitsky et al., *J. Clin. Micro.* 20:211-216, 1985). Mouse serum downregulates the activation of human and mouse cells by numerous different PAMPs (pathogen associated molecular patterns) in addition to LPS, and pre-incubation of cells in mouse but not human serum followed by washing the cells and subsequent stimulation also results in downregulation of the cells. The serum factors are unlikely to function by binding and detoxifying LPS, or by specifically influencing the TLR-4 signaling mechanism. This implies a limited role by complement and by lipoproteins like HDL, LDL and VLDL, which appear to detoxify LPS following binding (Feingold et al., *Infect. Immun.* 63:2041-2046, 1995; Freudenberg and Galanos, *Eur. J. Biochem.* 152:353-359, 1985; Ulevitch, *Adv. Immunol.* 53:267-289, 1993; Ulevitch and Johnston, *J. Clin. Invest.* 62:1313-1324, 1978).

A limited role of serum factors that influence the LPS-TLR4 interaction, like LPS-binding protein (LBP), soluble CD14 (sCD14) and MD2 in the observed variation in cell activation within different sera is also indicated. First, adding LBP to mouse or human plasma does not change the TNF response of PEM in vitro at high (>5%) serum percentage (Heumann et al., *Infect. Immun.* 69:378-385, 2001). Second, differences in endothelial cell activation are not altered by adding sCD14. This is important, as endothelial cells do not express mCD14 and are therefore dependent on sCD14 in serum to induce a response to LPS (Haziot et al., *J. Immunol.* 151:1500-1507, 1993). Last, sMD-2 is unlikely to play a role in the observed difference in serum activity, because MD-2 associates with TLR-4 in the endoplasmic reticulum in cells that express both MD-2 and TLR-4 (Visintin et al., *Proc. Natl. Acad. Sci. USA* 98:12156-12161, 2001). The cells used in these experiments express both MD-2 and TLR-4 (Akashi et al., *J. Immunol.* 164:3471-3475, 2000; Talreja et al., *Immu-* nology 113:224-233, 2004). Although this cannot exclude a role for MD-2, in combination with the serum action on different PAMPs it makes the role for MD-2 unlikely. Without being bound to a particular theory, these findings suggest that the action of serum on cytokine responses are likely working on a downstream intracellular factor, which connects multiple cell activation pathways.

EXAMPLE 2

The Effects of Serum from Other Species

Despite the known differences in LPS susceptibility between species, two commonly used animal models for LPS research are rodents and baboons, both LPS-resistant species. Multiple strategies for treating sepsis in experimental models may have had disappointing results in humans, an LPS-sensitive species, because of this difference. The use of more sensitive animals, such as rabbits or sheep, might therefore be a more reliable model to study sepsis pathology.

Lethal Dose 50

Lethality rather than other LPS induced effects in vivo, e.g., changes in body temperature or cardiac symptoms, were studied. To quantify the lethal effects of LPS in different animals, literature references for LD50 doses were used where available. A search on MEDLINE (database publicly available at the website of the National Center for Biotechnology Information (NCBI), Bethesda, Md.) was performed to find the 50% lethality dose (LD50) for LPS for the following animals: mice, cattle, rats, hamsters, guinea pigs, dogs, turtles, chickens, rabbits, rhesus monkeys, sheep, and horses. Combinations of the following keywords were used: LPS, lipopolysaccharide, endotoxin, LD50, lethal dose 50, lethal dose, mouse, mice, human, fetal calf, cattle, rats, hamster, guinea pig, dogs, canine, turtle, chicken, rabbit, rhesus monkey, sheep, and horse. Relevant papers were retrieved and additional articles identified from the reference lists of these papers. LD50 doses following intravenous LPS injection were preferred over intraperitoneal or other injection routes. If multiple LD50 doses were found, concentrations were averaged. If no intravenous LD50 dose was found, the LD50 dose for other injection routes was used without compensating for the different route, as is true in mice (Lehmann et al., *J. Exp. Med.* 165:657-663, 1987). All doses were converted into mg LPS/kg bodyweight.

Where LD50 values were not available, assumptions were made to complete the correlation analysis. The LD80 dose for rabbits was assumed to be sufficiently close to the LD50 dose, as there is only a small difference between these doses in dogs (Clark, *Trans. R. Soc. Trop. Med. Hyg.* 76:47, 1982; Maclean and Weil, *Circ. Res.* 4:546-556, 1956). Some LD50 doses were estimated by averaging the lowest LD100 dose and the highest known dose without lethality (see below). To increase the accuracy of the LD50 doses used for analysis, other in vivo LPS effect endpoints, such as fever, were compared between animals (van Deventer et al., *Blood* 76:2520-2526, 1990; Ohtsulka et al., *J. Vet. Med. Sci.* 59:1075-1077, 1997; Begley et al., *Am. Rev. Resp. Dis.* 130:1140-1146, 1984; Peel et al., *Infect. Immun.* 58:439-442, 1990). The doses for these endpoints were in a similar range and therefore consistent with the LD50 doses used. While some animals become more sensitive to LPS with age (e.g., humans) (Clark, *Trans. R. Soc. Trop. Med. Hyg.* 76:4-7, 1982; Gabriel et al., *Exp. Gerontol.* 37:235-247, 2002), LD50 doses were not age-corrected as these differences are small compared to differences in LPS sensitivity between species. Finally, the LPS LD50 dose for turtles was based on the LPS LD50 dose for lizards, as they are both reptiles. Removing the turtle data from the analysis did not alter our results significantly. If no estimation could be made, the animal was excluded from the correlation analysis.

LPS LD50 doses were found for guinea pigs (McCuskey et al., *Infect. Immun.* 45:278-280, 1984), hamsters (Prendergast et al., *J. Biol. Rhythms* 18:51-62, 2003), mice (Reynolds et al., *J. Endotoxin. Res.* 8:307-314, 2002) and rats (Clark, *Trans. R. Soc. Trop. Med. Hyg.* 76:4-7, 1982; McCuskey et al., *Infect. Immun.* 45:278-280, 1984) and dogs (Clark, *Trans. R. Soc. Trop. Med. Hyg.* 76:4-7, 1982). For the following animals, an LD100 was found: cattle (Clark, *Trans. R. Soc. Trop. Med. Hyg.* 76:4-7, 1982), chickens (Jones and Kiesow, *Infect. Immun.* 10:1343-1349, 1974), humans (Taveira da Silva et al., *N. Engl. J. Med.* 328:1457-1460, 1993) and sheep (Golenbock et al., *Infect. Immun.* 55:2471-2476, 1987) and LPS doses at which no deaths were described (van Deventer et al., *Blood* 76:2520-2526, 1990; Ohtsuka et al., *J. Vet. Med. Sci.* 59:1075-1077, 1997; Smith et al., *Res. Vet. Sci.* 24:154-160, 1978; Begley et al., *Am. Rev. Resp. Dis.* 130:1140-1146, 1984). To estimate the LD50 dose for rhesus monkeys, a LD100 dose for baboons (Hinshaw et al., *Surg. Gynecol. Obstet.* 147:545-557, 1978) and a LPS dose at which no deaths were described for rhesus monkeys (Clark, *Trans. R. Soc. Trop. Med. Hyg.* 76:4-7, 1982) were averaged. For rabbits an LD80 concentration for LPS was used as an LD50 (Garcia et al., *Crit. Care Med.* 22:1211-1218, 1994). No data was found on turtle lethality after injection of LPS. As no harm was described in lizards after an injection of 200 mg LPS/kg (Clark, *Trans. R. Soc. Trop. Med. Hyg.* 76:4-7, 1982); this was used as an LD50 for turtles. No in vivo data on horse lethality in response to TNF was found. The LPS LD50 doses used for further analysis are listed in Table 3.

TABLE 3

| Animal | LD50 mg/kg |
| --- | --- |
| Human | 0.007* |
| Sheep | 0.01* |
| Calf[1] | 0.03* |
| Rabbit | 0.1** |
| Dog | 0.5 |
| Guinea Pig | 0.8 |
| Hamster | 10 |
| Rat | 12 |
| Monkey[2] | 14* |
| Mouse | 15 |
| Chicken | 183* |
| Turtle | 200*** |

*LD50 was estimated by averaging the lowest LD100 found with the highest [LPS] describing no deaths
**LD80 mg/kg
***No harm caused at this dose for lizards
[1]no difference was made between calves and cattle
[2]No difference was made between baboons and rhesus monkeys Mouse, Baboon, and Chicken Sera Inhibit Production of TNF from Elicited Mouse Peritoneal Macrophages Decades ago, low concentrations of serum were observed to facilitate the growth of many cultured cells, presumably because the serum provides a more physiological microenvironment for cellular growth and/or supplies nutrient(s). Cow serum was used initially, however, this serum contains IgG which confounded some experiments. Serum from baby calves (fetal calf serum, FCS), which is low in IgG, is therefore preferred. FCS at a concentration of 5-10% has evolved into common use for cell cultures, a choice that appears to have been empiric.

Figure 8:
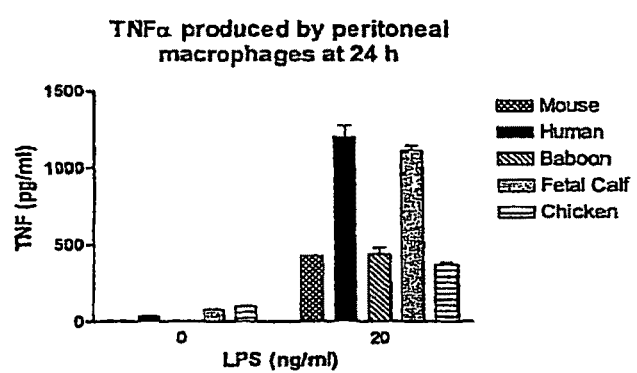
FIG. 8 is a graph showing TNFα production by peritoneal macrophages in the presence 20 ng LPS/ml or absence of LPS incubated in sera from mouse, human, baboon, fetal calf, or chicken. LPS-sensitive species (human and fetal calf) exhibit higher TNFα production than LPS-resistant species (mouse, baboon, and chicken).

To study the effects of serum from different species, sera from two LPS-sensitive animals (humans and fetal calves) were compared with sera from three LPS-resistant animals (mice, baboons, and chickens). Sera from fetal calf, chickens, and rodents was obtained commercially as described herein, and human sera was obtained from volunteers. A small amount of baboon sera was received as a gift from Dr. Keith Mansfield at the New England Primate Center. The amount of TNF produced by elicited peritoneal macrophages was determined after 24 hours in the presence of 10% of each sera. Cells incubated in the presence of the sera of the two LPS-sensitive animals produce more TNF (FIG. 8). These findings have been repeated in several different forms.

Mouse PEM TNF Production

To examine the effect of serum from different species on cytokine production in response to LPS stimulation, mouse peritoneal exudative macrophages (PEM) were stimulated with increasing concentrations of LPS in media with or without 5% serum of various species. Production of TNF in response to serum alone was only observed with guinea pig serum, which yielded 825 pg TNF/ml without LPS stimulation. Otherwise, in the absence of serum at least 200 ng LPS/ml was required for TNF production.

Figure 9:
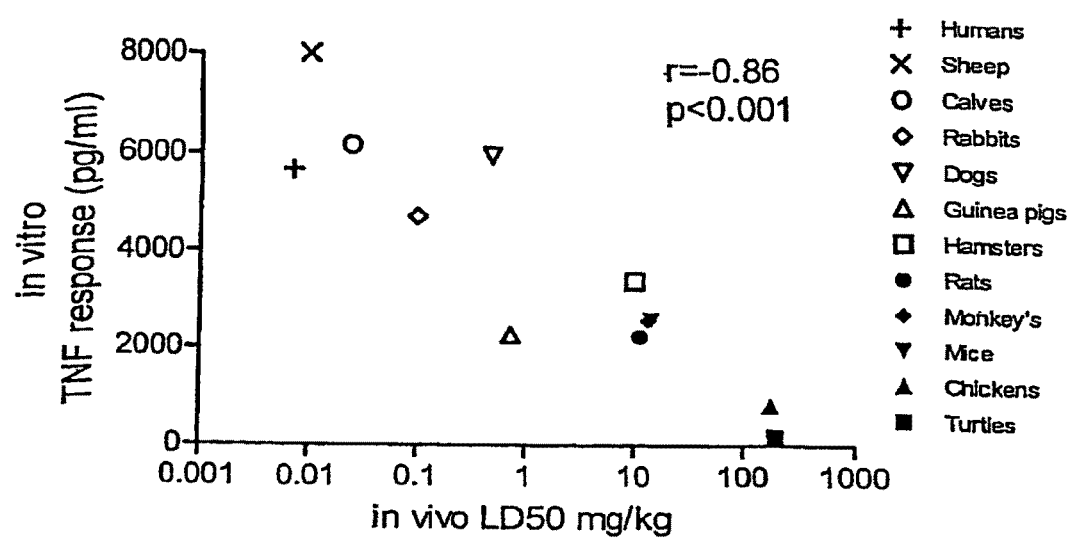
FIG. 9 is a graph showing a correlation between the in vivo lipopolysaccharide (LPS) LD50 dose of various species and the effect of their serum on production of Tumor Necrosis Factor (TNF) by peritoneal exudative macrophages (PEM), assayed by in vitro stimulation with 20 ng LPS/ml in 5% serum.

When 5% serum was added, significant variation in TNF production was observed between the different sera which correlated with in vivo lethality of LPS. The strongest correlation followed cell stimulation with 20 ng LPS/ml ($r=-0.86$, $p<0.001$) (FIG. 9). The degree of correlation varied between different LPS doses (Table 4).

TABLE 4

Correlation between effect of serum on mouse PEM cytokine response and in vivo LD50 of corresponding animals

| | | LPS Concentration | | | | | | | |
|---|---|---|---|---|---|---|---|---|---|
| | | 2 ng/ml serum percentage | | 20 ng/ml serum percentage | | 200 ng/ml serum percentage | | 2000 ng/ml serum percentage | |
| Cytokines | Parameter | 5% | 20% | 5% | 20% | 5% | 20% | 5% | 20% |
| TNF | Spearman r | −0.80 | −0.69 | −0.86 | −0.93 | −0.54 | −0.85 | −0.46 | −0.36 |
| | P value (two-tailed) | ** | * | *** | *** | ns | *** | ns | ns |
| IL-6 | Spearman r | −0.49 | −0.31 | −0.75 | −0.62 | −0.35 | −0.52 | 0.00 | −0.10 |
| | P value (two-tailed) | ns | ns | ** | * | ns | * | ns | ns |

*$p < 0.05$
**$p < 0.01$
***$p < 0.001$

Effects of Sera from a Variety of Species on Mouse and Human Macrophage Cells

The serum of animals sensitive to LPS (e.g., human, chimpanzee, cow, horse, pig, hamster, guinea pig, and rabbit) likely facilitates the induction of pro-inflammatory cytokines from cells, whereas the serum of animals resistant to LPS (e.g., mouse, rat, baboon, chicken, and lizard) likely suppresses the induction of cytokines from these species. These results contribute to the understanding of the comparative physiology of bacterial toxins. One approach is to use LPS alone as the stimulus with only mouse peritoneal macrophages or human PBMCs. The results can be confirmed using other PAMPs in other human cells or endothelial cells.

Because small variations in the TNF production in different mouse strains likely reflect differences in cellular response, sera from both strains of mice may equally and strongly suppress TNF from the different cells studied.

Sera obtained from commercial sources may be heavily contaminated with LPS, and such sera from an LPS-sensitive animal alone may be sufficient to induce cytokine production from the cells. Each serum can be tested for LPS content by a *Limulus* Amoebocyte Lysate test, using the heat and dilution techniques to remove inhibitory factors (Novitsky et al., *J. Clin. Micro.* 20:211-216, 1985). Testing the limited number of cytokines by ELISA is preferred as this technique is more easily individualized and more flexible when the experimental conditions are changed. In another embodiment, multiplex bead technology can be used, either in place of or in addition to ELISA.

Figure 10:
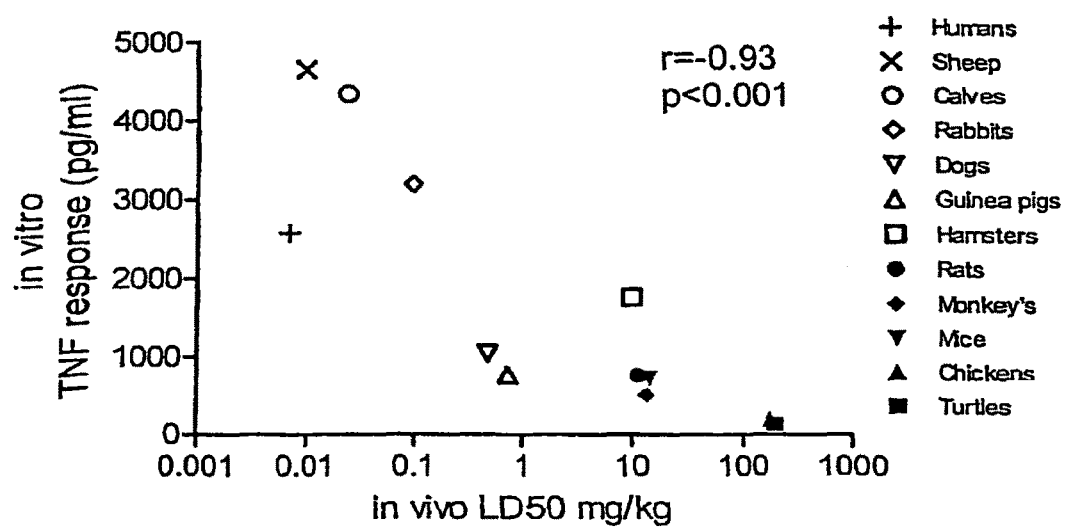
FIG. 10 is a graph showing a correlation between the in vivo LPS LD50 dose of various species and the effect of their serum on production of TNF by PEM, assayed by in vitro stimulation with 20 ng LPS/ml in 20% serum.

At the highest concentration of LPS (2000 ng LPS/ml) no significant correlation could be observed. Using 20% serum, variations in production of TNF correlating with in vivo lethality were observed (Table 4). Again the highest correlation with in vivo lethality was found with the TNF response to 20 ng LPS/ml ($r=-0.93$ $p<0.001$) (FIG. 10). Production of TNF was significantly lower when stimulated in 20% serum as compared to 5% serum, suggesting an inhibiting effect of serum.

IL-6 was not produced using any sera in the absence of LPS (data not shown). PEMs stimulated with LPS produced varying concentrations of IL-6, depending on the origin of the serum. A correlation between in vivo production of IL-6 was present after stimulation with 20 and 200 ng LPS/ml (Table 4). Cells stimulated in 20% serum produced similar or lower IL-6 concentrations compared to 5% serum, depending on the serum and LPS dose. No differences in cytotoxicity were observed between the sera studied, as assayed with crystal violet (data not shown).

Mouse Bone Marrow Derived Macrophage (BMDM) TNF Production

BMDM were stimulated with doses of LPS ranging from 2 ng/ml to 2000 ng/ml in serum from various species. After stimulation with more than 2 ng LPS/ml in the presence of various sera, variations in TNF production correlated to in vivo LPS induced lethality (Table 5). Cell activation with 20 ng LPS/ml ($r=-0.82$ $p<0.01$) resulted in the highest correlation.

TABLE 5

Correlation between effect of serum on mouse BMDM TNF
response and in vivo LD50 of corresponding animals

| | | LPS concentration | | | | | | | |
|---|---|---|---|---|---|---|---|---|---|
| | | 2 ng/ml serum percentage | | 20 ng/ml serum percentage | | 200 ng/ml serum percentage | | 2000 ng/ml serum percentage | |
| Cells | Parameter | 5% | 20% | 5% | 20% | 5% | 20% | 5% | 20% |
| BMDM | Spearman r | −0.50 | −0.10 | −0.82 | −0.65 | −0.62 | −0.64 | −0.65 | −0.53 |
| | P value (two-tailed) | ns | ns | ** | * | * | * | * | ns |

*p < 0.05
**p < 0.01
***p < 0.001

No differences were seen in cytotoxicity between the sera, as assayed by crystal violet.

Human Umbilical Vein Endothelial Cells (HUVEC)

HUVEC in serum of various species were stimulated with doses of LPS, ranging from 2 ng/ml to 2000 ng/ml. In the absence of serum no production of IL-6 could be measured, presumably due to the lack of mCD14 on endothelial cells (Frey et al., *J. Exp. Med.* 176:1665-1671, 1992; Pugin et al., *Proc. Natl. Acad. Sci. USA* 90:2744-2748, 1993; Von Asmuth et al., *Immunology* 80:78-83, 1993).

Figure 11:
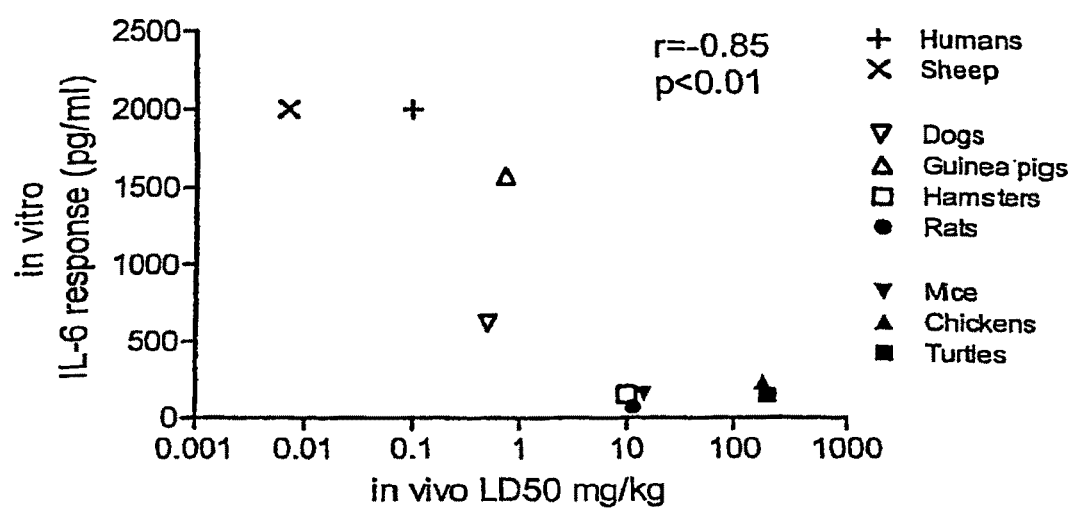
FIG. 11 is a graph showing a correlation between the in vivo LPS LD50 dose of various species and the effect of their serum on production of IL-6 by HUVEC, assayed by in vitro stimulation with 200 ng LPS/ml in 5% serum.

With 5% serum, but no LPS, IL-6 production was observed between 65 pg/ml (mouse serum) and 200 pg/ml (dog serum) (FIG. 11). A minimal increase in IL-6 production above the background level of less than 200 pg/ml was seen with 2 or 20 ng LPS/ml. Stimulation with 20 ng LPS/ml or more generated a variation in IL-6 production which correlated with in vivo LPS sensitivity (Table 6). The production of IL-6 was higher in the presence of 20% serum, as compared to 5% serum (data not shown).

flected by differences in TNF production). The correlation may reflect a relationship between the inhibiting effect of serum on cell activation and LPS induced lethality. Because the immune system is capable of inducing harmful effects, limitation of this response is therapeutically beneficial.

EXAMPLE 3

Purification of an Inflammation Response Modulator

Protein purification techniques involving a chromatofocusing step together with a cell based assay of LPS-induced TNF production may be used to purify the TNFα production-inhibiting substance from serum, e.g., mouse serum. The assay system may readily be optimized for sensitivity, rapid turn-around time, and ease. In particular, the active inhibitory fractions may be separated into fractions using chromatofocusing of a 40-60% ammonium sulfate precipitation, as described below. Samples can be studied by SDS-PAGE and,

TABLE 6

Correlation between effect of serum on HUVEC IL-6
response and in vivo LD50 of corresponding animals

| | | LPS concentration | | | | | | | |
|---|---|---|---|---|---|---|---|---|---|
| | | 2 ng/ml serum percentage | | 20 ng/ml serum percentage | | 200 ng/ml serum percentage | | 2000 ng/ml serum percentage | |
| Cells | parameter | 5% | 20% | 5% | 20% | 5% | 20% | 5% | 20% |
| HUVEC | Spearman r | 0.10 | 0.23 | −0.70 | −0.43 | −0.85 | −0.87 | −0.81 | −0.39 |
| | p value (two-tailed) | ns | ns | * | ns | ** | ** | * | ns |

*p < 0.05
**p < 0.01
***p < 0.001

LPS Sensitivity is Mediated by Serum Factor(s)

The above experiments demonstrate a striking correlation between in vivo induced LPS lethality and in vitro TNF and IL-6 production by mouse macrophages after LPS stimulation in serum of different species, with a maximum correlation coefficient of −0.93 (p<0.001) found on PEM TNF production after activation with 20 ng LPS/ml in 20% serum. These findings indicate that serum factors are likely important in species sensitivity to LPS. In all sera, less cytokine production was observed when macrophages were stimulated in an increasing serum concentration, indicating an inhibiting effect of serum on the immune response of macrophages to LPS. The inhibiting effect was concordant with findings of Heumann et al. (*Infect. Immun.* 69:378-385, 2001). The inhibitory activities differed between the sera studied (reif necessary, by two-dimensional analysis. Candidate protein fractions are assessed by mass spectrometry and/or microsequenced and the results are compared to known and predicted sequences, including mouse sequences.

Figure 12:
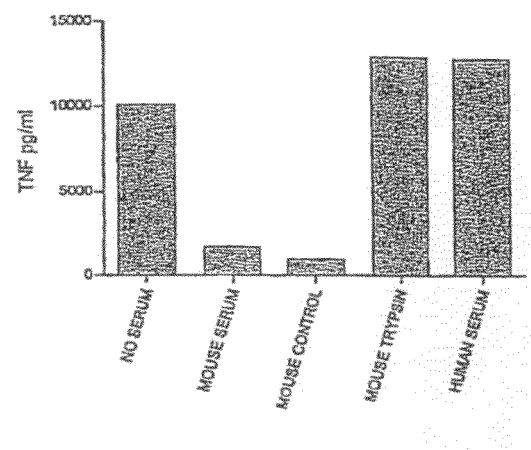
FIG. 12 is a graph showing TNF production in mouse serum is increased when treated with trypsin, indicating that the inhibitory factor is likely a protein.
Figure 13:
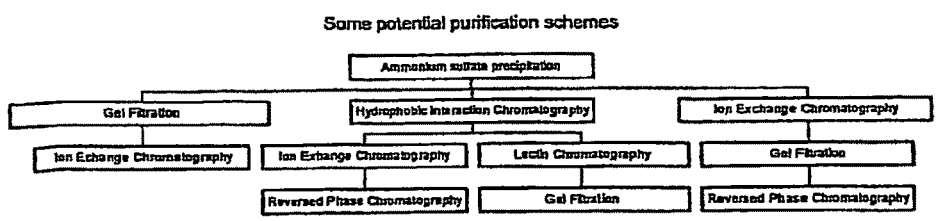
FIG. 13 is a diagram showing an exemplary purification strategy for the inhibitory factor present in mouse serum.

Exposure of Mouse Serum to Trypsin Removes all Inhibitory Activity, Indicating that the Inhibitory Substance is a Protein To determine whether the active compound(s) in mouse serum may be a protein, mouse and human serum were incubated overnight at 37° C. in the presence or absence of sepharose beads covalently coupled to trypsin (Pierce Chemical). Sepharose beads without trypsin were used as a control. The beads were then removed from the serum by centrifugation. Peripheral blood mononuclear cells (PBMCs) were prepared and washed in RPMI media containing no serum. This media was then replaced with media containing 5% of each of the sera shown. The cells were then stimulated with LPS at 1 ng/ml for 24 hours, after which the supernatants were collected and assayed for TNF (FIG. 12). As expected, TNF release was inhibited by RPMI media with 5% mouse serum and with 5% mouse serum preincubated with control sepharose beads (labeled mouse control in FIG. 12). In contrast, TNF release in RPMI media with 5% of the trypsin-exposed mouse serum was similar to RPMI media with no serum or media with 5% human serum. The results indicate that trypsin removes the inhibitory activity of mouse serum on TNF production, and suggest that the inhibitory substance in mouse serum is a protein. This experiment has been done twice with similar results.

Purification Steps

The starting material for purifying the active principle in mouse serum consists of pools of commercially acquired mouse serum (Antibodies Inc. Davis, Calif.) that may be prepared and frozen in aliquots as appropriate. This serum has similar activity as that prepared directly from mice and remains active for at least 6 months at 4° C. The purification may require as much as several liters of mouse serum. All experiments and fractionations should be performed in strictly pyrogen-free conditions with pyrogen-free buffers and highly purified water, and all glassware should be baked to remove potentially contaminating LPS. Desirably a HPLC machine devoted to pyrogen-free separations is used.

The activity that modulates an inflammatory response precipitated from mouse serum at between 40% and 60% ammonium sulfate saturation (repeated four times). Material remaining in the supernatant at 40%, but precipitating at 60% was used as the starting material for the experiments described below. The active compound(s) passed through a sulphopropyl strong cation exchange column (SP Sepharose fast flow, Amersham Biosciences) (performed three times). The active compound(s) was retained on a quaternary ammonium strong anion exchange column (Q Sepharose fast flow, Amersham Biosciences), and was eluted between 280 and 380 (e.g., at 330) mM NaCl (performed seven times). The active compound(s) was eluted from a gel filtration column (HPLC, Superose 6) with an apparent molecular weight of approximately 150 kD (performed three times), although this molecular weight may be of a multimer of the active compound(s) or may reflect the presence of another compound or compounds bound to the active compound. The active compound(s) did not contain IgG as determined by Western blotting. The active compound(s) was retained on a Con A Sepharose 4B lectin column and is eluted with 0.5 M α-D-methylglucoside (performed two times), suggesting that the protein is glycosylated. The active compound(s) eluted from a C4 reverse phase HPLC column run with water and acetonitrile at an acetonitrile concentration of 74%. The active compound(s) eluted from a hydroxyapatite column between 0.05 and 0.15 M $PO_4$ buffer (e.g., 0.10 M $PO_4$ buffer). The active compound(s) is stable over months at 4° C.

In particular, using chromatofocusing of the 40-60% ammonium sulfate precipitation, there was considerable purification, with two peaks of activity at pH 5.2+/−0.1 and pH 4.5+/−0.1. As such, there may be two proteins responsible for the activity. The early peak at pH 5.2 was partially purified, and found to be a mixture of proteins. The second peak (the one at pH 4.5) was further purified using high pressure liquid chromatography on a MonoQ anion exchange column. This step yielded considerable further purification, and the isolated proteins, which eluted at approximately 200+/−10 mM NaCL, are approximately 5-6 proteins, based upon re-purification on the MonoQ column, analytical sizing chromatography, and SDS gel electrophoresis analysis. Of these 5-6 proteins, about 90% was a single protein of approximately 75-90 kD on SDS silver stained gels (just above the mouse albumin band). Two much fainter bands at approximately 43-45 kD and a still fainter band at approximately 25 kD were also visible on SDS silver stained gels. Further mass spectrometry analysis indicated that the isolated proteins were predominantly hemopexin, human keratin (a contaminant), vanin-3, transthyretin, and dermcidin. Hemopexin is likely to be an active anti-inflammatory compound in mouse serum.

In addition, alpha-fetoprotein was purified from mouse serum using the method described above. Alpha-fetoprotein may also be purified from mice as described, for example, in Olsson et al. (The Journal of Experimental Medicine 145: 819-827, 1977), from humans, as described, for example in Yachnin et al. (Biochim. Biophys. Acta. 493:418-428, 1977), and human alpha-fetoprotein is commercially available, for example, from Cell Sciences (Canton, Mass.) under catalog number CRA206A.

Hemopexin is a serum glycoprotein that binds haem and transports it to the liver for breakdown and iron recovery, after which free hemopexin returns to circulation (Tolosano and Altruda, DNA Cell Biol. 21:297-306, 2002). Hemopexin prevents haem-mediated oxidative stress. Structurally hemopexin consists of two similar halves of approximately two hundred amino acid residues connected by a histidine-rich hinge region. Each half is itself formed by the repetition of a basic unit of some 35 to 45 residues. Hemopexin-like domains have been found in two other types of proteins, vitronectin (Yoneda et al., Biochemistry 5:6351-6360, 1998), a cell adhesion and spreading factor found in plasma and tissues, and matrixins MMP-1, MMP-2, MMP-3, MMP-9, MMP-10, MMP-11, MMP-12, MMP-14, MMP-15 and MMP-16, members of the matrix metalloproteinase family that cleave extracellular matrix constituents (Das et al. Mol. Cell. Biochem. 253:31-40, 2003). These zinc endopeptidases, which belong to the MEROPS peptidase database peptidase subfamily M10A, have a single hemopexin-like domain in their C-terminal section. The hemopexin domain may facilitate binding to a variety of molecules and proteins, for example the HX repeats of some matrixins bind tissue inhibitor of metallopeptidases (TIMPs). Polypeptides that have or contain the amino acid sequence of (or a sequence that is substantially identical to the sequence of) GenBank Accession No. AAA58678 (*Homo sapiens*), NP_000604 (*Homo sapiens*), AAH19901 (*Mus musculus*), or NP_445770 (*Rattus norvegicus*), or a fragment thereof, may be used in the methods of treatment and the compositions described herein.

The Vanin family represents a class of secreted or membrane-associated ectoenzymes that may be involved in processes pertaining to tissue repair in the context of oxidative stress (Matrin et al., Immunogenetics 53:296-306, 2001). Polypeptides that have the amino acid sequence of (or a sequence that is substantially identical to the sequence of) GenBank Accession No. ABA60895 (*Homo sapiens*), CAC33872 (*Homo sapiens*), AAI11522 (*Mus musculus*), CAB59323 (*Mus musculus*), or XP_574282 (*Rattus norvegicus*), or a fragment thereof, may be used in the methods of treatment and the compositions described herein.

Transthyretin is a tetrameric protein associated with the most common form of systemic amyloid disease (Keetch et al., J. Biol. Chem. 280:41667-41674, 2005). Polypeptides that have the amino acid sequence of (or a sequence that is substantially identical to the sequence of) GenBank Accession No. NP_000362 (*Homo sapiens*), NP_038725 (*Mus musculus*), or NP036813 or CAA70449 or NP_036813 (*Rattus norvegicus*), or a fragment thereof, may be used in the methods of treatment and the compositions described herein.

Dermcidin has been characterized as a neuron survival-promoting peptide that may operate by diffusion to regulate the immune response and thereby rescue neurons that would usually degenerate after cortical lesions and may also have direct neuron survival-promoting effects due to its phosphatase activity (Cunningham et al., J. Neurosci. 18:7047-7060, 1998). In addition, dermcidin has been characterized as an antimicrobial peptide (Harder and Schroder, Chem. Immunol. Allergy 86:22-41, 2005). Polypeptides that have or contain the amino acid sequence of (or a sequence that is substantially identical to the sequence of) GenBank Accession No. NP_444513 (*Homo sapiens*), AAH69108 (*Homo sapiens*), AAL18349 (*Homo sapiens*), or AAN63881 (*Rattus norvegicus*), or a fragment thereof, may be used in the methods of treatment and the compositions described herein.

Alpha-fetoprotein is one of the major plasma proteins in mammalian fetuses, but disappears almost entirely after birth. Alpha-fetoprotein plays a role in normal embryogenesis and in various diseases. Alpha-fetoprotein is known to bind and transport a multitude of ligands such as bilirubin, fatty acids, retinoids, steroids, heavy metals, flavonoids, phytoestrogens, dioxin, and various drugs. Mammalian alpha-fetoprotein has also been shown to regulate growth in a variety of in vitro (cell) and in vivo (animal) models (see, e.g., Mizejewski, Exp. Biol. Med. 226(5):377-408, 2001). Polypeptides that have or contain the amino acid sequence of (or a sequence that is substantially identical to the sequence of) GenBank Accession No. EAX05681 (*Homo sapiens*), AAH27881 (*Homo sapiens*), AAA37189 (*Mus musculus*), NP_031449 (*Mus musculus*), CAD86790 (*Mus musculus*), AAH66206 (*Mus musculus*), NP_036625 (*Rattus norvegicus*), CAA24567 (*Rattus norvegicus*), or AAH97344 (*Rattus norvegicus*) or a fragment thereof may be used in the methods of treatment and the compositions described herein.

Macrophage Assay for the Purification

The macrophage assay has been optimized and streamlined for high sensitivity, small volumes, and rapid turnover of results. Any type of macrophage (e.g., induced peritoneal macrophages) may be used for this assay; however, mouse bone marrow macrophages are preferred and are now routinely used. The cells can be prepared in large numbers, frozen in aliquots and have less day-to-day variation than the RAW cell line. The cells can be prepared and stimulated with a fixed concentration of LPS on a sensitive portion of the dose response curve in the presence of separated fractions of mouse serum. Fractions can be added to pre-prepared and slightly concentrated media to prevent dilution. Supernatants can be tested by ELISA for TNF, and fractions that suppress the production of TNF can be pooled for subsequent purification. Routine controls for the assay may include no LPS, LPS with no added fractions, and starting material with known suppressing activity. Results may be verified with a full dilution series of LPS, and with dilutions of active suppressing fractions to provide better measurements of the potency of the factor. To ensure that the compound purified from mouse serum reproduces the results observed with whole serum, active fractions may be tested to ensure that they suppress IL-6 production. Similarly, the active fractions may be tested for cytokine suppression using other stimuli, e.g., killed whole bacterial cells, to eliminate the possibility that the purified compound binds and neutralizes LPS, rather than acting at the cellular level. Activation of mouse or human macrophages by LPS may require LPS binding protein (LBP) for optimal signaling. If insufficient TNF is induced from the cells by the added LPS, small amounts of fetal calf serum or purified LBP (Biometec, Greifswald, Germany) may be added as a source of LBP. However, good activation of both mouse and human cells signaling was observed without serum or exogenous LBP, using either LPS or other PAMPs. Thus, it is not desirable to add LBP, as an LBP-dependent signal would not reflect signaling from other PAMPs. As noted herein, mouse serum from LBP KO mice also suppresses TNF in the assay.

In another embodiment, a PAW other than LPS may be used (which would not be affected by LBP) to stimulate the cells in the assay. As the factor acts on the cells when pre-incubated (see data herein), physical interaction of the protein with the stimulant may not be required. In yet another embodiment, the cells may be pre-incubated with the fractions, washed, and then stimulated with LPS to remove LBP from the assay. This may avoid confounding effects of the possible presence LBP in the fractions from the assay.

Analysis of Hepatoma Cell Line Supernatant

The mouse hepatoma cell line (Hepa 1-6) was initially derived from the BW7756 tumor in the C57L mouse. Cells were grown in DMEM medium (Dulbecco's Modified Eagle's Medium) containing 10% fetal calf serum and then weaned to 5% fetal calf serum without difficulty. The medium in which hepatoma tumor cell lines have been cultured contains high concentrations of alpha-fetoprotein.

Previously prepared murine bone marrow derived macrophages (BMDMs) were cultured overnight at a cell density of 1.2 million cells, after which the cells were washed and incubated with different test samples at a volume of 25 microliters in the presence or absence of LPS at a final concentration of 200 ng/ml in a final volume of 100 microliters in a 96-well tissue culture plate. The test samples contained: conditioned media from the hepatoma cell line, media containing 5% mouse sera, media containing 5% fetal calf serum sera, and a subset of these samples that had been previously exposed to trypsin coupled beads to confirm that the active principle in the media or mouse serum was protein. For the preparation of the trypsin exposed samples, conditioned cell line medium, and separately 5% mouse serum, were incubated overnight in the presence of trypsin coupled beads (Pierce), after which the samples were centrifuged twice and then filtered to remove the trypsin coupled beads. These samples were included with the test samples. All test samples were incubated with the BMDM cells overnight at 37° C. After 18 hours of cell culture, the cell supernatants were harvested and tested for tumor necrosis factor (TNF) by ELISA.

Figure 17:
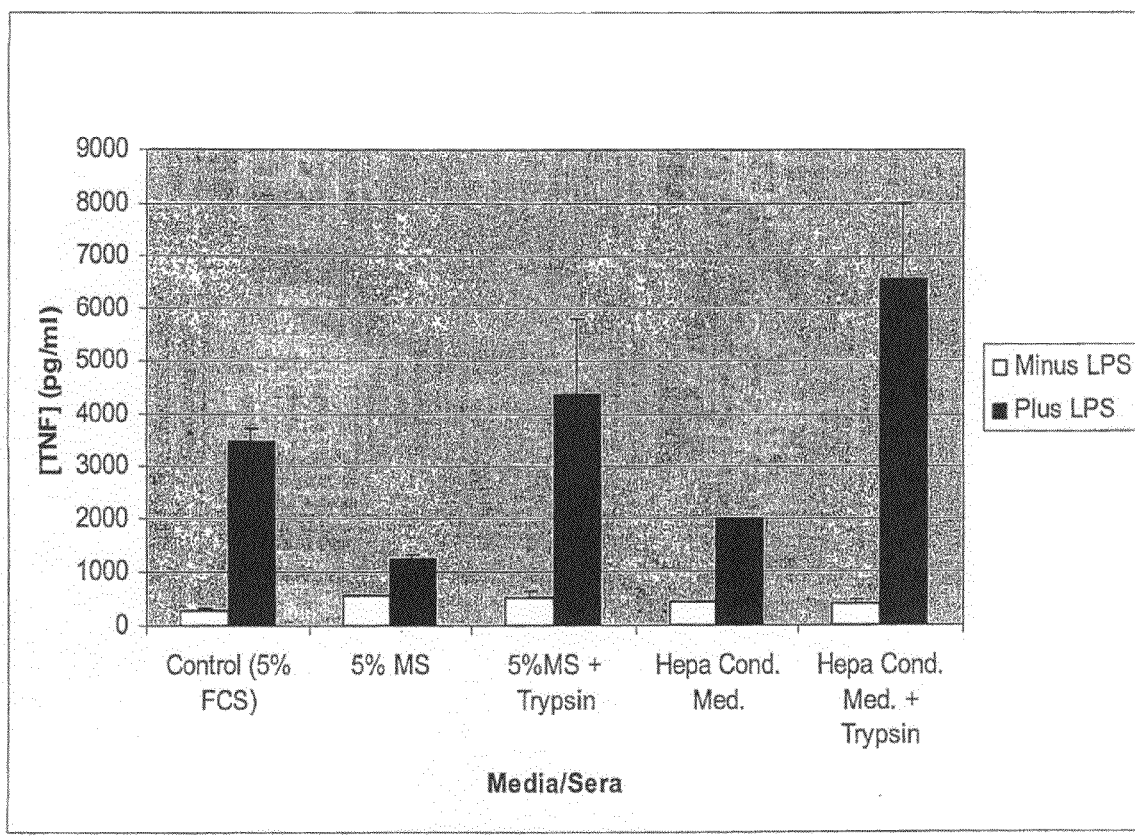
FIG. 17 is a graph showing that mouse serum (5%) and conditioned hepatoma cell line culture supernatant inhibit the production of LPS-induced TNF in murine bone marrow derived macrophage (BMDM) cells. The open bars depict results obtained without the addition of LPS and the solid bars depict results obtained with the addition of LPS.
Figure 18:
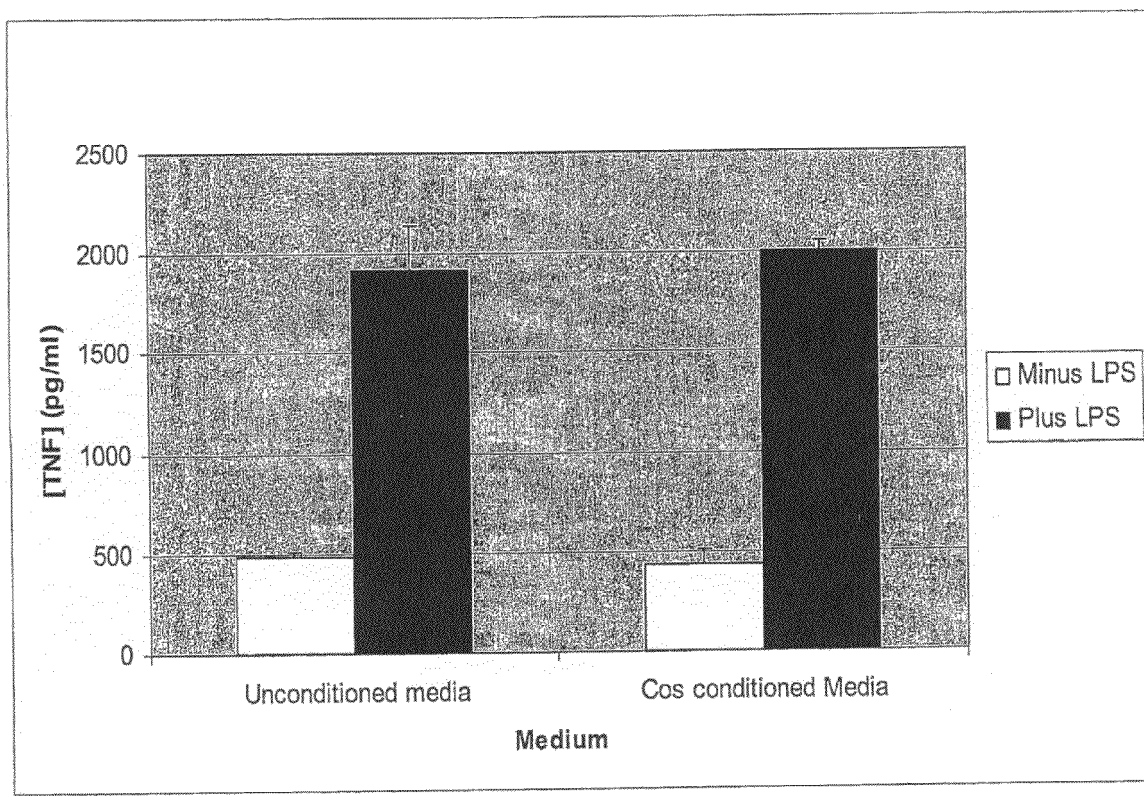
FIG. 18 is a graph showing that supernatants obtained from COS cells (simian fibroblasts (CV-1 cells) transformed by SV40 virus lacking the origin of replication), in the absence or presence of LPS did not inhibit the production LPS-induced TNF in murine BMDM cells. The open bars depict results obtained without the addition of LPS and the solid bars depict results obtained with the addition of LPS.

These results, as indicated in FIG. 17, show that 5% mouse serum and the conditioned hepatoma cell line culture supernatant inhibit the production of LPS-induced TNF from BMDM cells. As expected, there was no inhibition in the samples containing medium with 5% fetal calf serum. Previous exposure of the conditioned cell line supernatant or the mouse serum to trypsin coupled beads removed inhibiting activity, indicating that the active compound(s) is/are protein. As an additional control, in a separate experiment, supernatants from COS cells, generated and tested in an identical manner in the presence and absence of LPS, did not show any inhibitory activity (FIG. 18).

Figure 19:
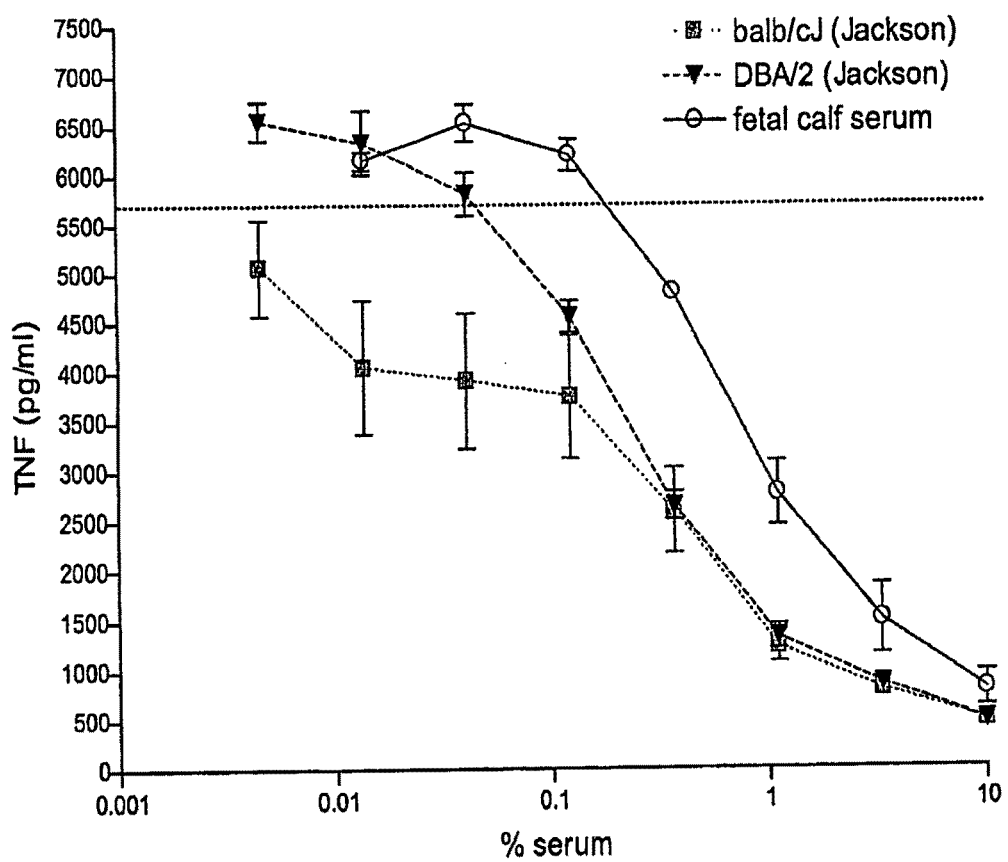
FIG. 19 is a graph showing TNF production by murine BMDM cells in different sera. Results obtained using sera from Balb/CJ mice is shown using filled-in squares; results obtained using sera from DBA/2 mice is shown using solid triangles; and results obtained using fetal calf serum is shown using open circles.

To further test this concept, 5 Balb/CJ mice were purchased (Jackson). Balb/CJ mouse markedly overproduces alpha-fetoprotein (see, e.g., Olsson et al., The Journal of Experimental Medicine 145:819-827, 1977). 5 DBA/2 mice, which do not overproduce alpha-fetoprotein, were also purchased (Jackson). The mice were bled and the inhibitory activity of the sera were studied in the same assay as above. Specifically, BMDMs were cultured overnight as above, and then stimulated with LPS at a fixed concentration of 200 ng/ml LPS and varying dilutions of the sera from the two mouse stains in media. Dilutions of calf serum were also studied as a control. The results are shown in FIG. 19. The sera from the Balb/CJ mice, mice that overproduce alpha-fetoprotein, significantly inhibited the TNF response compared to the control DBA/2 mouse sera. As expected, sera from both mouse strains inhibited the production of TNF relative to the dilutions of fetal calf serum. The results are plotted as the mean of 5 different sera. In FIG. 19, the dotted line indicates the production of TNF when the cells were stimulated with LPS in media that contained no serum.

Analysis of the Fractions

Progress of the purification may be monitored at intervals by determining the activity of the protein as estimated by dilution resulting in 50% suppression of TNF divided by total protein. As some proteins lose activity with increasing purity due to conformational changes or exhibit increased susceptibility to trace proteases, it may be desirable to add the active fractions into constant, low, known concentrations of albumin and/or add exogenous protease inhibitors. Samples may be assessed for purity by SDS-PAGE or two-dimensional analysis using iso-electric focusing as the second dimension. Active fractions containing a limited number of proteins may be further assessed by identifying each of the proteins in the mixture, for example, using mass spectrometry or microsequencing. Results can be compared to known and predicted sequences, e.g., mouse sequences.

Nevertheless, as suppression of a cytokine response is profound even with large (microgram/ml) doses of LPS and extends to stimuli such as entire killed bacteria, contamination of the fractions with trace amounts of LPS is unlikely to be a detriment.

Uses of the Compound(s) from Mouse Serum that Suppresses Production of TNF from Mouse Cells Further purification of the factor(s) in mouse serum which suppresses a cytokine response can lead to strategies to neutralize its effect (e.g., modulating compounds identified by screening). In addition, the identification of the responsible factors enable the production of new mouse models for the study of sepsis that more closely resemble human physiology and may provide reagents for more precise study of its cellular mechanism(s) of action (See the heading below, entitled "Determination at What Level Suppression of Cell Signaling Occurs").

Moreover, hemopexin (or a polypeptide containing a hemopexin domain), vanin-3, transthyretin, dermcidin, or alpha-fetoprotein may be added to mammalian serum to reduce or prevent an inflammatory response in cells contacted with the serum. Desirably, the serum is human or fetal calf serum.

EXAMPLE 4

Cell Signaling Effects of the Active Compound(s)

The effects of the mouse serum (and purified compounds) on several key points in the signaling cascade (FIG. 14) may be studied to determine at what level of cell signaling the suppression by mouse serum occurs. Mouse serum alters p38 MAP kinase, erk1/2, and NF-κB activation in human monocytes in response to LPS. In particular, the effect of mouse serum on purified mouse peritoneal and bone marrow derived macrophages and human peripheral blood monocytes may be studied at the following levels of signaling: p38 MAPK, erk1/2, NF-κB activation, TLR expression, MyD88/IRAK complexes, IRAK-1 and IRAK-4 kinase activity, IRAK-M, IκBα degradation, activation of STAT3 and SP-1, and mRNA for TNF.

Figure 15:
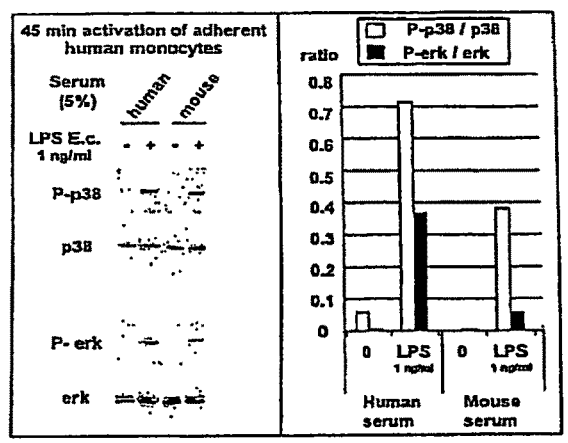
FIG. 15 is a graph showing activation of adherent human monocytes after 45 minutes in human or mouse sera (5%) either in the presence (1 ng/ml) or absence of LPS.

Mouse Serum Alters p38 MAP Kinase, erk1/2, and NF-κB Activation in Human Monocytes in Response to LPS Western blot analysis using cytoplasmic extracts of human monocytes stimulated for 45 minutes with LPS in the presence of 5% human or 5% mouse serum was performed. Specific anti-p38, anti-phosphorylated p38, anti-erk1/2, and anti-phosphorylated erk1/2 were used to develop the blots. The level of activation of both kinases, illustrated by the increased expression of the phosphorylated forms of p38 and erk, was increased with human serum (FIG. 15). These experiments, performed twice, indicate that the signaling pathways leading to the activation of p38 MAP kinase and erk1/2 are less strongly initiated in the presence of mouse serum relative to human serum.

The effects of mouse and human serum on the activation of NF-κB after stimulation with LPS were compared. Human PBMCs were purified using Ficoll-Hypaque. Monocytes were selected by adherence and stimulated with 10 ng/ml *E. coli* 0111:B4 LPS for 45 minutes in the presence of 10% human or mouse serum. Nuclear extracts were prepared, and NF-κB activation was assessed by electrophoretic mobility shift assay (EMSA) as described (Adib-Conquy et al., *Am. J. Respir. Crit. Care Med.* 162:1877-1883, 2000) (FIG. 16).

After LPS activation strong nuclear translocation was obtained in the presence of 10% human serum, whereas NF-κB activation was less strong in the presence of 10% mouse serum. Supershift analysis allowed the identification of the two bands corresponding to inactive homodimer p50p50 and active heterodimer p50p65, respectively (data not shown). Mouse serum appears to limit expression of both forms of NF-κB, consistent with the hypothesis that mouse serum interferes with PAMP-induced activation of the signaling cascade.

Figure 16A:
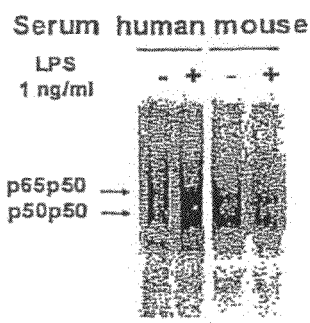
FIGS. 16A, 16B, and 16C are gel images and graphs showing nuclear NF-κB analyzed by electrophoretic mobility shift assay (EMSA) in human monocytes in human or mouse sera either in the presence of 1 ng/ml LPS or absence of LPS.
Figure 16B:
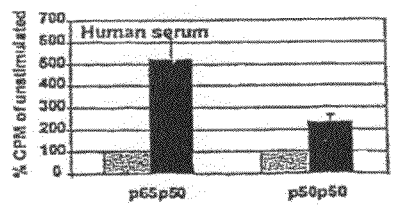
Figure 16C:
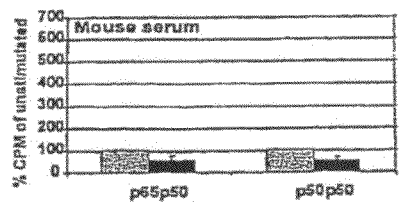

This experiment has been performed twice with similar results. FIG. 16A is representative of one experiment, and FIGS. 16B and 16C (showing % CPM of unstimulated cells on the Y axis) show the mean of both experiments.

Determination at What Level the Suppression of Cell Signaling Occurs

The cytokine response modulation present in mouse serum may decrease nuclear translocation of NF-κB in LPS-activated macrophages. The point in the signaling cascade where suppression occurs can be determined. Multiple steps of signaling from the cell surface to mRNA expression can be examined. Because mouse serum may suppress TNFα while increasing the anti-inflammatory cytokine IL-10, the signaling pathway of IL-10 can be studied. Thus, the effects of mouse serum, human serum, and the candidate purified factor(s) from mouse serum (i.e., hemopexin, vanin-3, transthyretin, alpha-fetoprotein, and dermcidin) on cellular signaling can be compared.

Figure 14:
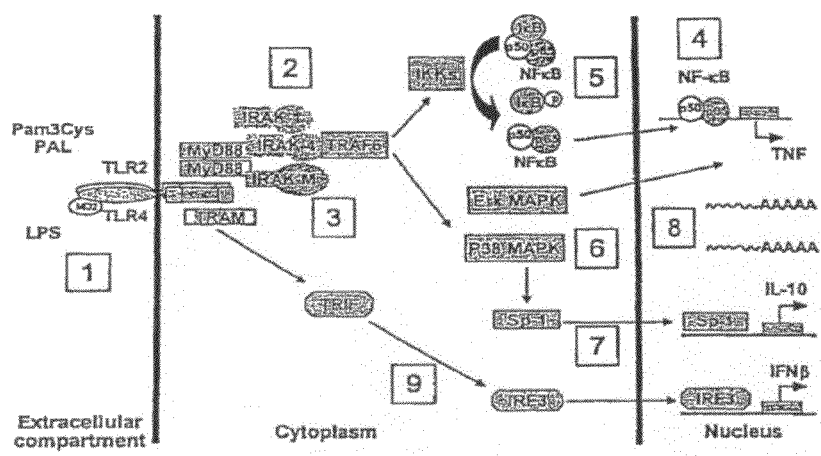
FIG. 14 is a diagram showing possible signaling pathways that can be studied in the presence of different sera to determine at what level the suppression of cell signaling occurs in the presence of the inhibitory factor (e.g., in mouse serum). The numbers in boxes in this figure correspond to the numbered items in the "Materials and Methods" section of the Detailed Description, unless noted otherwise.

Except as indicated, the signaling in both human peripheral blood monocytes and elicited mouse peritoneal macrophages can be studied, using either LPS, Pam3Cys, or heat killed *E. coli* to activate the cells to provide several different pathways of stimulation. FIG. 14 provides examples of different points of the signaling cascade. Methods for these studies are described in the "Materials and Methods" section below.

The downregulation of Toll-like receptors (TLRs) at the surface of monocytes can be investigated. Modulation by mouse serum of TLRs on the cell surface of monocytes can be analyzed using flow cytometry to measure surface expression of TLR2 and TLR4.

In addition, defects in the formation of the MyD88/IRAK complexes and inhibition of IRAK-1 and IRAK-4 kinase activity can be investigated. Mouse serum may induce changes in the intracellular signaling pathway leading to NF- κB activation. In an endotoxin tolerance model, a defect in the formation of the MyD88/IRAK-1 complex and IRAK-1 kinase activity (Li et al., *J. Biol. Chem.* 275:23340-23345, 2000) was associated with IRAK-1 degradation. Some immunostimulatory cytokines such as IFNγ and GM-CSF prevented endotoxin tolerance by inhibiting IRAK-1 degradation (Adib-Conquy and Cavaillon, *J. Biol. Chem.* 277:27927-27934, 2002). However, the kinase activity of IRAK-1 is not necessary for signal transduction, because kinase-inactive mutants of IRAK-1 induce NF-κB activation (Knop and Martin, *FEBS Lett.* 448:81-85, 1999; Maschera et al., *Biochem. J.* 339:227-231, 1999). IRAK-4 can also induce NF-κB activation, but its activation potential depends on its kinase activity. Furthermore, IRAK-4 can phosphorylate IRAK-1 (Li et al., *Proc. Natl. Acad. Sci. USA* 99:5567-5572, 2002).

The expression of IRAK-M, a negative regulator of pro-inflammatory cytokines identified using knock-out mice, can also be analyzed. These mice exhibit increased TLR/IL-1R signaling, and their macrophages produced higher cytokine levels in response to TLR ligands or killed bacteria than wild-type mice (Kobayashi et al., *Cell* 110:191-202, 2002).

The activation of transcription factors such as NF-κB can be measured in the monocytes and macrophages by EMSA as described, for example, by Adib-Conquy et al. (*Am. Respir. Crit. Care Med.* 162:1877-1883, 2000) using supershift analysis to identify the nature of the bands.

The effects on IκBα degradation can also be studied. Suppression by mouse serum may be mediated by a stabilization or absence of degradation of the IκBα, an inhibitor of NF-κB nuclear translocation, as described in an experimental model for endotoxin tolerance (LaRue and McCall, *J. Exp. Med.* 180:2269-2275, 1994). In the minutes following stimulation, IκBα is rapidly phosphorylated and degraded, allowing NF-κB nuclear translocation. The effect of mouse serum, as compared to human serum, on the kinetics of IκBα degradation can be followed.

The effects of mouse sera on activation of p38 and erk MAP kinase can also be studied. Activation of p38 MAP kinase (p38 MAPK) is necessary in addition to NF-κB and erk for TNF production; inhibition of p38 MAPK leads to a defective TNF release (Foey et al., *J. Immunol.* 160:920-928, 1998). Thus, p38 MAPK may be important for a pro-inflammatory pathway, although p38 MAPK may also be involved in IL-10 induction (Adib-Conquy et al., *Am. J. Respir. Crit. Care Med.* 168:158-164, 2003; Ma et al., J. Biol. Chem. 276:13664-13674, 2001).

Further, the effects of mouse sera on IL-10-related signaling molecules can be investigated. In conjunction with TNF-inducing signaling pathways, the effect of mouse sera on the activation of transcription factors necessary for IL-10 production can be analyzed, including STAT3 and Sp-1. In contrast to TNF, mouse sera increases the production of IL-10 by monocytes and macrophages. STAT3 is necessary for the activation of IL-10 promoter (Benkhart et al., *J. Immunol.* 165:1612-1617, 2000), whereas Sp-1 plays a key role in the induction of IL-10 in monocyte/macrophages (Brightbill et al., *J. Immunol.* 164:1940-1951, 2000).

The effects on TNF, IL-1, IL-6, and IL10 mRNA transcription can also be studied. Mouse serum and/or the purified compound(s) may alter transcription of cytokines.

The MyD88 independent pathway can also be studied. Interferon-β is induced by LPS using a MyD88 independent pathway requiring the adaptor molecules TRAM and TRIF and the nuclear factor IRF3 (Yamamoto et al., *Science* 301:640-643, 2003).

Negative regulatory signaling molecules (e.g., SOCS1, Tollip, ST2, SIGIRR, and MyD88s) can be studied. Such regulatory molecules (Nakagawa et al., *Immunity* 17:677-687, 2002; Burns et al., *Nat. Cell Biol.* 2:346-351, 2000; Brint et al., *Nat. Immunol.* 5:373-379, 2004; Wald et al., *Nat. Immunol.* 4:920-927, 2003; Janssens et al., *Curr. Biol.* 12:467-471, 2002) have been described to play a role in the downregulation of the TLR signaling pathway. Further, for the case of enhancement of any of the negative molecules, results can be confirmed using appropriate KO mice.

While the suppression may be due to the downregulation of TLRs, this is less likely. For instance, the alteration of NF-κB activation was observed less than one hour after incubation with mouse serum, which excludes effects at the transcriptional level. The inhibition of TNF production was found with many PAMPs that are not TLR4 agonists, implying that several different TLRs are downregulated at the same time. While unlikely, rapid internalization of the receptors may be a mechanism of inhibition.

EXAMPLE 5

Animal Models

The present invention encompasses animal models, for example, animals that have an altered inflammatory response (e.g., severe sepsis, or autoimmune diseases such as rheumatoid arthritis or inflammatory bowel disease). Exemplary animal models include animals in which the activity of a compound (i.e., hemopexin, vanin-3, transthyretin, alpha-fetoprotein, and/or dermcidin) is reduced by the administration of an antibody that specifically binds the compound (e.g., an antibody that binds the compound of interest at a higher affinity than any other compound), as well as knockout and transgenic animals. Knockout animals may be generated, for example, to create mice with enhanced susceptibility to PAMPs such as LPS. Desirably these knockout animals lack expression of hemopexin (or a protein containing a hemopexin polypeptide), vanin-3, transthyretin, alpha-fetoprotein, or dermcidin. Alternatively, transgenic animals may be generated, for example, to create mice with enhanced resistance to septic shock. Without limitation, particularly preferred are knockout or transgenic animals in which the inflammation response phenotype is fully penetrant and/or the lifespan of the knockout or transgenic animal is not shortened by a knockout- or transgene-related pathology.

Generation of Knockout and Conditional Knockout Animals

Methods for production of knockout animals are standard in the art. The generation of knockout animals may provide a valuable tool for investigation of the human inflammation response. In one example, a mouse model for studying sepsis and inflammation diseases such as inflammatory bowel disease and rheumatoid arthritis, lacking the gene encoding hemopexin (e.g., one having a sequence encoding AAH119901 (*Mus musculus*)), or a protein containing a hemopexin polypeptide, is generated. However, other genes may also be used to produce knockout mice provided that they are compatible with the mouse genome and that the protein encoded by this gene is able to carry out the function of inflammation response modulating compound(s).

In addition, the knockout organism may be a conditional knockout. For example, either the FRT/FLP system or the Cre-lox system may be used to generate conditional knockout animals. The use of the FLP/FRT system is standard in the art and is described in, for example, U.S. Pat. No. 5,527,695, and Lyznik et al. (*Nucleic Acids Res.* 24:3784-3789, 1996). The Cre-lox system is standard in the art and is described in, for example, Kilby et al. (*Trends Genet.* 9:413-421, 1993).

Generation of Transgenic Animals

Transgenic animals, such as mice and rats, may be made using standard techniques; see, for example, Hammer et al. (*Cell* 63:1099-1112, 1990). For example, a gene encoding hemopexin (or a protein containing a hemopexin polypeptide), vanin-3, transthyretin, alpha-fetoprotein, or dermcidin may be provided using endogenous control sequences or using constitutive, tissue-specific, or inducible regulatory sequences. Any tissue specific promoter may direct the expression of the inflammation modulating compound(s) used in the invention, such as monocyte specific promoters, macrophage specific promoters, or endothelial cell specific promoters.

Construction of transgenes can be accomplished using any suitable genetic engineering technique, such as those described in Sambrook et al. (*Molecular Cloning: A Laboratory Manual*, Cold Spring Harbor Laboratory, N.Y., (1989)). Many techniques of transgene construction and of expression constructs for transfection or transformation in general are known and may be used for the constructs.

One skilled in the art will appreciate that a promoter may be chosen that directs expression of an inflammation modulating gene in the cells of the blood stream or bone marrow or other relevant tissues in which an inflammation response can develop. For example, any promoter that regulates expression of an inflammation inhibitor or enhancer in monocyte, macrophage, or endothelial cells can be used in the expression constructs of the present invention. Once a suitable transgene construct has been made, any suitable technique for introducing this construct into embryonic cells can be used.

Furthermore, a transgene, such as a mutant gene encoding for hemopexin (or a protein containing a hemopexin polypeptide), vanin-3, transthyretin, alpha-fetoprotein, or dermcidin may be conditionally expressed (e.g., in a tetracycline sensitive manner). The tetracycline regulatable system is well known to those skilled in the art and is described in, for example, WO 94/29442, WO 96/40892, WO 96/01313, and Yamamoto et al. (*Cell* 101:57-66, 2000).

Particularly preferred is a mouse model for the inflammation response wherein the gene encoding hemopexin (or a protein containing a hemopexin polypeptide), vanin-3, transthyretin, alpha-fetoprotein, or dermcidin is expressed in, for example, monocyte, macrophage, or endothelial cells of the transgenic mouse such that the transgenic mouse exhibits an altered inflammation response. In addition, relevant cell lines (e.g., monocyte, macrophage, or endothelial cells) from these mice may be established by methods standard in the art. Animals suitable for knockout and transgenic experiments can be obtained from standard commercial sources such as Taconic (Germantown, N.Y.).

Use of Animal Models

Knockout and transgenic animals, as well as animals in which the activity of hemopexin (or a protein containing a hemopexin polypeptide), vanin-3, transthyretin, alpha-fetoprotein, or dermcidin has been reduced by the administration of an antibody that specifically binds one of these proteins, may be used as research tools to determine genetic and physiological features of inflammation, and for identifying compounds that can affect inflammation, sepsis, and inflammatory diseases such as inflammatory bowel disease and rheumatoid arthritis. Knockout animals also include animals where the normal gene (e.g., a gene encoding hemopexin (or a protein containing a hemopexin polypeptide), vanin-3, transthyretin, alpha-fetoprotein, or dermcidin) has been inactivated or removed and replaced with a mutant form of this gene, for example, a polymorphic allele. These animals can serve as a model system for assessing, for example, the susceptibility to septic shock upon PAMP administration associated with a particular mutation.

In model animals may be used in screens directed at analyzing expression of specific genes, for example, inflammation response can be assayed at varying concentrations of PAMPs (e.g., LPS). Expression can be monitored by immunohistochemistry as well as by protein and RNA blotting techniques. Knockout animals that are more sensitive to LPS and thus better approximate human physiology are particularly useful for these screens.

Further, model animals can also be used in an assessment of the effects of treatment paradigms (including the use of compounds identified as affecting sepsis) on differential gene expression (DGE). The information derived from the surveys of DGE can ultimately be correlated with inflammation in the knockout or transgenic animals. Again it is desirable to use knockout animals that better approximate human physiology in assaying a treatment paradigm.

EXAMPLE 6

Materials and Methods

The following materials and methods are used in the experiments described herein.

Sera

Serum was made from blood of male Balb/C mice (commercially purchased), male Sprague Dawley rats (commercially purchased), one female sheep (obtained as a kind gift of Dr. Warren Zapol, Dept of Anesthesia, Massachusetts General Hospital), female Golden Syrian hamsters (commercially purchased) and New Zealand White rabbits (commercially purchased). The blood was allowed to clot for at least six hours and centrifuged (Thermo IEC PR 7000). Serum was pipetted off and kept at 4° C. or frozen at −80° C. Rhesus monkey serum was obtained as a kind gift of Alan Cross, Department of Medicine, Center for Vaccine Development, University of Maryland, Baltimore, Md. Serum from the following animals: human (Lot #032K8938), dog (Lot #22K8937), turtle (Lot #26H9301) and guinea pig (Lot #063K8931) was commercially purchased in a powdered form, from Sigma Chemical, St Louis, Mo. Serum was made up in sterile water according to the manufacturer's instructions. Fetal calf serum was purchased from Abcys, Paris France, or Mediatech, Herndon, Va. Chicken serum (Lot #023K8401) was purchased from Sigma. Horse serum (Lot #449517) was purchased from Gibco.

Serum may be obtained from multiple sources to ensure that the results are generally relevant. Human and mouse serum may be purchased from commercial sources, obtained from human volunteers, or in some cases obtained from specific strains of mice as described. In this work, similar results were obtained with human and mouse sera from multiple different sources. One liter of pooled mouse serum was purchased from a single vendor and an additional liter was reserved (Antibodies Inc, Davis, Calif.). This serum is active in the assays described herein. Mouse serum devoid of sCD14 can be obtained from CD14 KO mice that are the kind gift of Mason Freeman (Massachusetts General Hospital, Boston, Mass.). Mouse sera from LBP and CD14 KO mice are also available at the Pasteur Institute (Paris, France). Fetal calf serum can be purchased from several commercial sources. Baboon serum has been obtained as the kind gift of Dr. Keith Mansfield, New England Primate Center. Serum from chickens, lizards, birds, rabbits, and sheep can be purchased from Sigma Cellular Activators Multiple microbial products, including LPS, bacterial lipoproteins, CpG DNA, lipoteichoic acid, and peptidoglycan and whole bacteria have been reported to stimulate inflammation. These different stimulants may be selectively used according to the goal of the experiments.

LPS

LPS derived from *Escherichia coli* O111:B4 was purchased from Sigma Chemical, St Louis, Mo. or List Co (Campbell, Calif.). LPS may be further purified to remove contaminating proteins (Manthey and Vogel, *J. Endotoxin Res.* 1:84-91, 1994). Milligram quantities of the former national reference endotoxin from *E. coli* O113 (EC5) that has been extensively characterized chemically and in human volunteers was available for the experiments described herein (Rudbach et al., *J. Clin. Microbiol.* 3:21-25, 1976).

Pam3Cys

Pam3Cys that has been synthetically manufactured may be purchased from EMC Microcollection, Tübingen, Germany and used as a TLR-2 agonist.

Peptidoglycan-Associated Lipoprotein (PAL)

PAL is an outer membrane protein involved in maintaining cell wall integrity (Lazzaroni and Portalier, *Mol. Microbiol.* 6:735-742, 1992; Vianney et al., *J. Bacteriol.* 178:4031-4038, 1996; Mizuno T., *J. Biochem.* 86:991-1000, 1979). PAL induces pro-inflammatory cytokines in low nanogram concentrations (Hellman et al., *J. Biol. Chem.* 277:14274-14280, 2002) and activates endothelial cells (unpublished data). PAL may be purified from *E. coli* as described in Hellman et al. (*J. Biol. Chem.* 277:14274-14280, 2002).

Flagellin

Flagellin from *E. coli* and *S. muenchen* may be purchased from Inotek (Beverly, Mass.). Material free of LPS by passage over anti-LPS columns may also be purchased from this vendor.

CpG DNA

Phosphodiester oligonucleotides, including activating oligodeoxynucleotide and non-activating oligodeoxynucleotide can be purchased from Sigma-Genosys.

Peptidoglycan (PG)

PG may be purchased from Toxin Technology (Sarasota, Fla.) and can be analyzed for contaminating LPS by LAL, and for contaminating outer membrane proteins by immunoblotting with anti-PAL, anti-MLP, and anti-OmpA antibodies.

Heat-Killed Bacteria

Heat-killed *E. coli* O111:B4 and *S. aureus* Cowan stain can be grown in appropriate broth, washed extensively by centrifugation, counted by dilution and plating on agar, killed by boiling, washed again, lyophilized, and weighed.

Preparation of Macrophage and Endothelial Cells

Standard protocols for several preparations of cells include the use of fetal calf serum. To determine the effect of this serum, cells may be first cultured in fetal calf serum, and then, after washing the cells, the media may be replaced with media containing one of mouse, human, and fetal calf serum, or no serum. Results from this procedure can be compared with harvesting or preparing cells using autologous serum in place of the fetal calf serum at each point. After washing the final preparation of cells, the media can be replaced with media containing one of mouse, human, and fetal calf serum, or no serum. Comparing these two methods allows determination of whether prior exposure of cells to fetal calf serum affects the results. C57Bl/6 or Balb/C mice may be used and results between the two strains can be compared. The use of Balb/C mice is preferred Macrophage Cells Mouse Peritoneal Exudative Macrophages (PEM)

Female C3H/HEN mice (commercially purchased at Charles River laboratories) were injected intraperitoneally with 1 mL of sterile 3% brewer's thioglycollate (Call et al., *Am. J. Pathol.* 158:715-721, 2001), 4-5 days later exudate macrophages were harvested. Mice were euthanized by $CO_2$ asphyxiation and peritoneal macrophages were obtained by peritoneal lavage with 10 mL of sterile DMEM culture media. Viable cells were counted by staining with trypan blue and plated in a 96-well plate at a concentration of $1.28 \times 10^6$ cells/ml DMEM culture media in 100 ml/well. Plates were cultured at 37° C., 5-10% $CO_2$ for 3-4 hours before being stimulated.

Mouse Bone Marrow Derived Macrophages

Bone marrow-derived macrophages (BMDMs) were prepared from mice according to the protocol described by Schilling et al (*J. Immunol.* 169:5874-5880, 2002). These cells can be frozen down in large numbers for use in multiple studies.

Femurs from female C57BL/6 mice were isolated after euthanasia by $CO_2$ asphyxiation. The ends of the femur were cut off, and, to flush out the stem cells, the femurs were washed with RPMI 1640 supplemented with 10% mouse, human or fetal calf serum, 1% Hepes, 1% penicillin/streptomycin (10,000 U/ml), sodium pyruvate (100 mM), 1% nonessential amino acids (10 mM), and 0.5% β-mercapthoethinol, penicillin, and streptomycin (basic BMDM media). Red blood cells were lysed with red blood cell lysis buffer obtained from Sigma. After washing of lysis buffer by spinning, viable cells were counted by staining with trypan blue and reconstituted in basic BMDM media supplemented with 0.50% fetal calf serum, 5% horse serum, 30% M-CSF (conditioned medium from cultures of L929 cells) (Weber et al., *J. Immunol.* 151:415-424, 1993), and 0.5% glucose (Differential media) to a concentration of $5 \times 10^6$ cells/30 ml basic medium supplemented with an additional 5% serum, 1.5 mM glucose, and M-CSF (30% conditioned medium from cultures of L929 cells) (Weber et al., *J. Immunol.* 151:415-424, 1993). Cells were cultured one week at 37° C., 5-10% $CO_2$ in pyrogen free bags (5×30 cm) made of hydrophobic Teflon foil (BioFOLIE, Sartorius).

After culturing, bags were checked for contamination by microscope. Cells were collected by sterile technique into a single pellet and reconstituted in cryoprotective media at $1.5 \times 10^7$ cells/ml and frozen at −80° C. Cells were transferred to liquid nitrogen for 3-7 days. Before stimulating, cells were thawed, reconstituted in basic BMDM media, and plated in a 96-well plate at a density of 400,000 cells/cm², and incubated overnight at 37° C., 5-10% $CO_2$. Alternatively, cells may be incubated for 7 days at 37° C., in 5% $CO_2$, harvested, and placed in wells of 48-well plates at a density of $4\text{-}6 \times 10^5/\text{cm}^2$ for 24-48 hours in to allow adherence. BMDMs may then be washed and stimulated in media containing either no serum or the same serum that the cells were harvested and cultured in.

Mouse Peripheral Blood Mononuclear Cells (MPBMCs)

MPBMCs can be prepared by centrifugation using Lympholyte M (Cedarlane, Ontario) according to the manufacturer's directions rather than Ficol. Cells may be counted as above and differential cell numbers determined by staining of aliquots. Purity of cells can be assessed by flow cytometry. Prior to use, media can be replaced with media containing no serum, or mouse, human or fetal calf serum.

RAW264.7 Mouse Macrophage Cell Line (RAW Cells)

RAW cells have been obtained from the American Type Culture Collection (ATCC) and are grown as specified by the ATCC. Cells can be maintained in the presence of 10% fetal calf serum or, as above, in autologous serum. Results from cells maintained in fetal calf serum may be compared with those maintained in autologous serum. Cells should not be passaged more that 10 times. Prior to the experiments, serum in the media may be replaced with media containing no serum, mouse serum, human serum, or fetal calf serum.

THP-1 Human Macrophage Cell Line (THP-1 Cells)

Because THP-1 cells are deficient in CD14 on their surface, a stably transfected cell line of THP-1 with CD14 may be used (Werts et al., *Nat. Immunol.* 2:346-352, 2001; originally obtained from R. Ulevitch (Scripps Clinic)). Cells can be grown and maintained in RPMI in the presence of fetal calf serum (or autologous serum), and washed and the media may be replaced with media containing no serum, mouse serum, human serum, or fetal calf serum for the experiments. Results obtained from cells maintained in fetal calf serum may be compared with those maintained in autologous serum.

Mouse Alveolar Macrophages (MAVs)

MAVs may be prepared essentially as described by Salez et al. (*J. Leukoc. Biol.* 67:545-552, 2000). Cells can be prepared from bronchoalveolar lavage fluid (8 washes of 0-5 ml each) from 7 week old mice immediately after sacrifice. Differential cell numbers may be assessed by staining of aliquots, and purity can be determined by FACS analysis.

Human Peripheral Blood Mononuclear Cells (HPBMCs)

HPBMCs can be prepared by Ficoll-Hypaque density gradient centrifugation. PBMCs may be washed and suspended in RPMI medium. In some experiments, after Ficoll-Hypaque centrifugation, monocytes may be prepared by aggregation at 4° C. followed by rosetting with sheep red blood cells (Petit-Bertron et al., *J. Leukoc. Biol.* 73:145-154, 2003; Armant et al., *J. Immunol.* 155:4868-4875, 1995). In other experiments, monocytes may be prepared by magnetic depletion of other cells using an anti-lineage antibody cocktail (CD7, CD19, CD45RA, CD56, and anti-IgE antibodies) and passage through a magnetic column. The flow through containing the enriched monocyte population may be centrifuged, and monocytes may be washed in medium. Cells may be plated in 96-well plates at a density of $5-6 \times 10^5$ cells/cm$^2$. Purity of cells can be determined by FACS analysis. The media may be replaced with media containing fetal calf, mouse, or human serum prior to stimulation.

Macrophage Experiments

Each type of cell may be grown under conditions indicated above and diluted to numbers appropriate for the system most commonly used for those cells (e.g., $2 \times 10^6$ cells/ml in 24 or 96 well plates). Media can be made up lacking serum or with 0.2% to 10% dilutions of fetal calf, mouse, or human serum. The cells can be stimulated in the presence of media containing each concentration of serum with dilutions of LPS, Pam3Cys, or beat killed *E. coli* for 4 and 20 hours, after which supernatants can be removed. Production of cytokines TNFα, IL-1β, IL-6, and IL-10 can be analyzed by ELISA and compared. Remaining supernatants can be frozen for future analysis.

Comparison of the Effects of Sera from a Variety of Species on Macrophage Cells.

Sera from each of the species can be obtained as described in the methods above or are available commercially. Macrophages from each source can be prepared as above and stimulated with dilutions of LPS in the presence of media containing 5% serum of each species. Production of cytokines TNF, IL-1β, IL-6, and IL-10 can be analyzed by ELISA and compared. Remaining supernatants can be frozen for future analysis, e.g., analysis using multiplex bead technology. Wild-type mouse species vary in their sensitivity to LPS. Accordingly, the modulation of sera obtained from two different strains of mice (Balb/c and C57Bl/6), which produce different amounts of TNF in response to a large intravenous LPS challenge may also be compared (Yamakawa et al., *Clin. Immunol. Immunopathol.* 79:256-262, 1996).

Comparison of Suppression by Different Sera

Peritoneal macrophages and HPBMCs can be stimulated in the presence of media containing one of fetal calf, mouse, and human serum, or lacking serum. Macrophages from each source can be prepared as above and stimulated with dilutions of heat killed Gram-negative and Gram-positive bacteria, synthetic TLR2 agonists (e.g., Pam3Cys and PAL), TLR-4 agonists (e.g., LPS), TLR-5 agonists (e.g., flagellin), and TLR-9 agonists (e.g., CpG DNA). Dilutions of each stimulus can be incubated with the cells in the presence of media lacking serum or containing 5% of either fetal calf, mouse, or human serum. Production of cytokines TNF, IL-1β, IL-6, and IL-10 can be analyzed by ELISA. Remaining supernatants can be frozen for future analysis.

Determination of Cytokine Suppression or Facilitation by a Variety of Sera

Peritoneal macrophages and HPBMCs can be prepared as above and stimulated with dilutions of LPS in the presence of media lacking serum or containing 5% of either fetal calf, mouse, or human serum. Supernatants can be tested immediately or frozen in aliquots at −80° C. until testing. The level or presence of cytokines may be assayed using multiplex bead technology (e.g., LincoPlex, St. Charles, Mo.), allowing simultaneous testing of numerous cytokines using very small sample volumes.

Endothelial Cells

Mouse Lung Endothelial Cells

Lung endothelial cells can be isolated from Balb/C mice by immunomagnetic isolation as described by Marelli-Berg et al. (*J. Immunol. Methods* 244:205-215, 2000). After exsanquination, both lungs may be excised, rinsed, cut into 2 mm$^3$ blocks, and washed by centrifugation. Tissue can be incubated in collagenase (0.5 mg/ml) for 1 hour at 37° C., and chunks can be removed by passage through a cell strainer. Digested/strained tissue can then be washed with PBS/2.5% FCS, suspended in trypsin/EDTA, and incubated at room temperature for 10 minutes. The resultant single cell suspension can then be washed with PBS/2.5% FCS by centrifugation, incubated with mouse IgG at 4° C. for 30 minutes to block Fc receptors, and washed again. Cells can then be incubated with a mixture of antibodies, including anti-mouse CD31, anti-mouse CD105; biotinylated isolectin B4 at 4° C. for 30 minutes; and washed by centrifugation. Pellets can be suspended in PBS/0.5% FCS supplemented with rat anti-mouse IgG and streptavidin-conjugated magnetic beads at 4° C. for 30 minutes. The resultant mix containing magnetically labeled and unlabeled cells can then be loaded onto a magnetic column (VarioMACS, Miltenyi Biotec), which is then washed with PBS/FCS and removed from the magnet. Cells can be eluted from the column with PBS/FCS, suspended in DMEM supplemented with glutamine, penicillin, streptomycin, sodium pyruvate, HEPES, nonessential amino acids, β2-mercaptoethanol, 20% FCS, EC growth supplement (Sigma), and heparin, and incubated at 37° C. under humidified $CO_2$ in gelatin coated tissue culture flasks. Prior to the start of the experiments, media can be replaced with fetal calf, human, or mouse serum.

Human Endothelial Cells

Human umbilical vein endothelial cells (HUVEC) and human lung microvascular endothelial cells (HMVEC-L) can be purchased Cambrex, East Rutherford, N.J. in cryopreserved form. They can be cultured at 37° C., 5-10% $CO_2$ for 4 days in endothelial cell basal media with any the following supplements: epidermal growth factor (EGF), fibroblast growth factor (FGF), vascular endothelial growth factor (VEGF), vitamin C, hydrocortisone, recombinant insulin-like growth factor (R3-IGF-1), heparin (HUVEC only), fetal calf serum and gentamicin/amphotericin B (supplemented according to the manufacturer's instructions for HUVEC media). Cells can be transferred into preconditioned media in flasks, and sub cultured when they reached ~80% confluence. The cells can be detached by short exposure to trypsin/EDTA, washed in sterile HUVEC media without serum or HBSS, suspended in the same media, placed in wells at a density of 60,000 cells/cm$^2$, and incubated overnight prior to adding stimulants. Because responsiveness can decrease with repeated passages, all experiments are performed using cells between the $2^{nd}$ and $5^{th}$ passage. Cryopreserved HUVEC arrive in their primary passage, whereas HMVEC-L generally arrive at passage 3 or 4.

Endothelial Cell Experiments

Activation of mouse and human endothelial cells by LPS, Pam3Cys, and killed *E. coli* in the presence of different sera may also be assayed. HUVEC cells may be used and results may be confirmed with human lung microvascular endothelial cells (HMVEC-L) and with mouse lung endothelial cells. Endothelial cells can be incubated with dilutions of each stimulant, no stimulant in the presence of media containing each sera alone, or TNFα (20 ng/ml, positive control). The read-out for endothelial cells may be, for example, the release or surface expression of adhesion molecules and the cytokines IL-6 and IL-8. Endothelial cell surface expression of E-selectin and P-selectin may be assessed at 1-2 hours by whole cell ELISA using, for example, a biotin avidin detection system to detect binding by the secondary antibody. Also, E-selectin levels and production of IL-6 and IL-8 in culture supernatants by ELISA may be measured (Appel et al., *Transplantation* 73:1302-1309, 2002).

Generation of Polyclonal Antibodies to the Mouse Inflammation Response Modulating Factor An IgG directed to hemopexin (or a protein containing a hemopexin polypeptide), vanin-3, transthyretin, alpha-fetoprotein, or dermcidin enables the development of an assay to quantify the protein in mice, to aid in purification or cloning of the protein, to deplete mouse serum of the protein in vitro and possibly in vivo, and to look for homologous proteins in other species. In one example, polyclonal antiserum to the mouse protein is generated in New Zealand white rabbits using purified protein. The initial immunization protocol consists of an initial intramuscular injection of 10-20 µg purified protein, followed by a boosting immunization 21 days later. Further boosts and/or the addition of adjuvant may be used if no or few antibodies are detected. Antibodies may be quantified by ELISA, analogous to that described (Siber et al., *J. Infect. Dis.* 152:954-964, 1985; Warren et al., *J. Infect. Dis.* 163:1256-1266, 1991). IgG may be purified from the rabbit antiserum, for example, by precipitation in 50% ammonium sulfate followed by affinity chromatography on Protein G sepharose 4B (Pharmacia).

Assays to Determine the Level at which Suppression of Cell Signaling Occurs

FIG. 14 illustrates the different points of the signaling cascade that can be studied. The numbers in boxes in FIG. 14 correspond to the number of the experimental methods below.

1. Downregulation of Toll-Like Receptors at the Surface of Monocytes

Human monocytes and mouse macrophages can be incubated for various times (1-18 hours) with mouse or human serum, washed, and then incubated with commercial anti-TLR antibodies coupled to FITC before analysis. Results may be expressed as percentage of cells expressing TLR2 or TLR4 and as mean fluorescence intensity, which indicates the level of expression of these receptors per cell.

2. Defect in the Formation of the MyD88/IRAK Complexes and Inhibition of IRAK-1 and IRAK-4 Kinase Activity IRAK-1 and IRAK-4 expression by Western-blot in monocytes or macrophages cultured in the presence or absence of human or mouse sera can be studied. In addition, IRAK-1 and IRAK-4 kinase activity can be measured in vitro using the myelin basic protein as a substrate of phosphorylation and also by measuring their autophosphorylation. IRAK-1 or IRAK-4 can be first immunoprecipitated from cellular extracts using specific antibodies and protein A sepharose. The immunoprecipitates can be incubated in kinase buffer in the presence of myelin basic protein and of $\gamma^{32}$P-ATP. The samples can be subjected to SDS-PAGE, the gels dried and the intensity of the radioactive signal quantified using a Storm® and the ImageQuant® software (Molecular Dynamics) (Adib-Conquy and Cavaillon, *J. Biol. Chem.* 277:27927-27934, 2002). IRAK-1 and IRAK-4 expression and kinase activity can be monitored after stimulation of the cells with LPS, the synthetic TLR2-specific agonist molecule Pam3Cys, and heat killed *E. coli*. Whole cell extracts can be prepared, and equal amounts of proteins separated by SDS-PAGE can be transferred onto nitrocellulose sheets and studied by Western blotting using specific commercial antibodies as described, for example, in Adib-Conquy and Cavaillon (*J. Biol. Chem.* 277:27927-27934, 2002).

3. Analysis of IRAK-M Expression

The expression of IRAK-M in monocytes or macrophages stimulated with LPS, Pam3Cys, or heat killed *E. coli* can be studied in the presence of mouse or human serum to determine if the presence of mouse serum increases the expression of this inhibitory molecule. The presence of IRAK-M in MyD88-associated complexes can be assessed by immunoprecipitation followed by SDS-PAGE and Western-blot, essentially as described, for example, in Adib-Conquy and Cavaillon (*J. Biol. Chem.* 277:27927-27934, 2002). Because the immunoprecipitation experiments require large numbers of cells, these experiments may be initially performed using the human monocytic cell line THP-1 stably transfected with CD14, and the murine macrophage-like cell line RAW 264-7. Once an alteration of the signaling pathway is identified, it can be confirmed that the same process occurs in primary human monocytes and mouse macrophages. IRAK-M KO mice can be used to confirm that IRAK-M is involved in the downregulation caused by the mouse serum protein, if desired (Kobayashi et al., *Cell* 110:191-202, 2002).

4. Effect on Activation of NF-κB and Other Transcription Factors

The activation of transcription factors can be measured in the monocytes and macrophages by EMSA as described, for example, in Adib-Conquy et al. (*Am. J. Respir. Crit. Care Med.* 162:1877-1883, 2000) using supershift analysis to identify the nature of the bands. A specific non-radioactive quantification such as TransAM™ (Active Motif) or Mercury TransFactor™ (BD Biosciences) can also be used. In these kits, the oligonucleotide corresponding to the transcription factor is immobilized on microtitration plates. The protein extracts are added to the wells. After washes, bound transcription factors can be detected in a colorimetric assay using specific antibodies coupled to peroxidase.

5. Effect on IκBα Degradation

Human monocytes or murine macrophages can be stimulated with LPS, Pam3Cys or heat killed *E. coli*, and whole cell extracts can be prepared at various times (up to 1 hour) after stimulation. IκBα expression and phosphorylation using antibodies specific for the phosphorylated form can be analyzed by Western-blotting, as described, for example, in Adib-Conquy and Cavaillon (*J. Biol. Chem.* 277:27927-27934, 2002). The comparison of total IκBα expression and of its phosphorylation allow determination of the inhibitory effect of mouse serum on activation of IκB kinases, or whether it acts at the level of IκBα degradation via the proteasome pathway. These results in this system can be confirmed in IκBα KO mice.

6. Effect of Mouse Sera on Activation of p38 and erk MAP Kinase

For these experiments, the human monocytes or mouse macrophages can be cultured in the presence or absence of human or mouse sera. The kinetics of p38 phosphorylation and erk can be monitored after stimulation with LPS, Pam3Cys, or heat killed *E. coli* using Western blotting as described, for example, in Adib-Conquy et al. (*Am. J. Respir. Crit. Care Med.* 168:158-164, 2003).

7. Effects of Mouse Sera on IL-10-Related Signaling Molecules

Human monocytes or mouse macrophages can be stimulated with LPS, Pam3Cys, or heat killed *E. coli*. Whole cell extracts can be prepared at various times (up to 1 hour) after stimulation. STAT3 activation can be assessed by Western-blot using antibodies against its phosphorylated form. Sp-1 activation can be analyzed by EMSA. Alternatively, specific non-radioactive quantification kits described above can be used.

8. Effect on TNF, IL-1, IL-6, and IL10 mRNA Transcription

The effects of mouse and human serum on the expression of mRNA for TNF, IL-1, IL-6, and IL10 can be compared by Northern blotting from the mouse or human cells as described, for example, in Hellman et al. (*J. Biol. Chem.* 277:14274-14280, 2002) and Adib-Conquy et al. (*Int. Immunol.* 11:689-698, 1999).

9. MyD88 Independent Pathway

Whether the MyD88 independent pathway is affected by the mouse serum protein can be tested by measuring the LPS-induced production of interferon β by ELISA. IRF3 may be studied by electrophoresis mobility shift assay, if desired (Wietek et al., *J. Biol. Chem.* 278:50923-50931, 2003).

10. Negative Regulatory Signaling Molecules (e.g., SOCS1, Tollip, ST2, SIGIRR, and MyD88s) (not Shown in FIG. 14)

Enhancement of these molecules can be investigated by mouse serum protein by PCR analysis. If desired, the appropriate KO mice where possible can be used to confirm results except for the case of MyD88s, which represents an alternative splicing.

Assays

Cytokine Assays

Mouse TNF concentrations were measured using a Duoset ELISA kit for mouse TNF (R&D Systems; Minneapolis, Minn.). The maximum mouse TNF concentration measured was 8 ng/ml. Human IL-6 concentrations were measured using Duoset ELISA kit for human IL-6 (R&D Systems; Minneapolis, Minn.). The maximum human IL-6 concentration measured was 2 ng/ml. ELISAs were performed following the manufacturer's protocol.

A mouse IL-6 sandwich ELISA was carried out using rat IgG anti-IL-6 as a capture antibody (R&D systems; Minneapolis, Min.) and goat IgG anti-IL-6 as a detection antibody (R&D Systems; Minneapolis, Minn.). The maximum mouse IL-6 concentration measured was 8 ng/ml. A similar protocol was used as for the R&D Duoset ELISA kit.

Crystal Violet Assay

Cells were stained by incubating in 0.5% crystal violet, 20% methanol for 30 minutes. They were washed with an excess of distilled water and allowed to dry. To develop, 100 μl of 100% methanol was added and plates were read at 550 nm with a universal microplate spectrophotometer (μQuant, BioTek Instruments Inc).

Experimental Design for Cytokine and Crystal Violet Assays

All cells were prepared as above and washed 3 times with their appropriate culture media. For culture media containing serum, was prepared without sera but was otherwise unchanged. Cells were stimulated with LPS for 18-20 hours at 37° C., 5-10% $CO_2$. LPS concentrations ranged from 2 ng LPS/ml to 2000 ng/ml. Cells were stimulated in sterile filtered culture media containing either 5% or 20% serum of species with different LPS sensitivity. Samples were prepared in duplicate. BMDM supernatants were analyzed for TNF. HUVEC supernatants were analyzed for IL-6, because they do not produce TNF. PEM supernatants were analysed for both TNF and IL-6 concentrations. Cytokine production in the absence of LPS was not subtracted from cytokine production after LPS stimulation.

After removing supernatants, cells were stained with crystal violet to assay cytotoxicity.

Statistical Analysis

General

P values<0.05 were considered statistically significant. Data was analyzed using the computer software program "GrapbPad Prism."

Correlation

Non parametric (Spearman) correlation was calculated between the LPS LD50 dose from multiple species and in vitro production of cytokines in the presence of corresponding serum. The average TNF or IL-6 production per serum was used. Two tailed p values were calculated for statistical significance.

In Vitro Experiments

Samples may be run at least in triplicate for in vitro studies. For most experiments T tests, the Wilcoxson test, or analysis of variance (ANOVA) are used to calculate the statistical significance of results. In addition, a post-hoc test can be performed when ANOVA indicates overall statistical significance.

Human Subjects Involvement and Characteristics

Blood can be collected from up to 100 healthy human volunteers, age ≥18 years. Blood can be fractionated into cellular and non-cellular components which can be used to compare the effects of certain proteins in human serum with those in mouse serum on human and mouse cells. Exclusion criteria may include infection within the last 4 weeks, and history of immune dysfunction. Only blood may be taken, which can be separated into cellular and non-cellular components.

Mouse Protocols

Experiments can be performed with Balb/C or C57Bl/6 mice (approximately 20 g). Up to 300 mice may be needed to generate sufficient macrophages for purification assays. All mice can be used for in vitro experiments in which macrophages and/or blood can be harvested from the peritoneum or bone marrow after euthanasia. The cells or blood can stimulated with the LPS or other stimulants in vitro, and serum can be prepared from the blood as well. Larger volumes of mouse blood may also be used to provide a source from which a mouse factor can be purified.

In general the use of inbred mice (e.g., Balb/C mice) should lead to more uniform results. As this strain is commonly used, these results can be compared with other studies. Also, this strain of mouse produces slightly more TNF in response to an in vivo LPS challenge than C57Bl mice (Yamakawa et al., *Clin. Immunol. Immunopathol.* 79:256-262, 1996). The effects in any of the above-described experiments of serum and cells from Balb/C mice with C57Bl/6 can be compared to ensure that there are no dramatic differences between these mouse strains. While it is more desirable to use mice for these assays, as the validity of the currently-used macrophage assays that use fetal calf serum and mouse macrophages as well as the validity of using mice to mimic human disease from bacterial toxins is assessed, the RAW cell tissue line can also be used.

In some experiments, mice may be injected intraperitoneally with thioglycollate five days prior to sacrifice to increase and alter the types of cells in the peritoneal cavity. This is a standard technique. Five days later these mice can be humanely sacrificed and cells can be obtained after sacrifice. For all other experiments involving the harvest of cells from other tissues, the mice can be humanely sacrificed prior to obtaining the cells (e.g., euthanized by $CO_2$ asphyxiation using compressed $CO_2$).

Rabbit Protocols

New Zealand male white rabbits (2.5-3 kg) can be used for all experiments. Rabbits can be vaccinated with a purified mouse protein (e.g., a protein that inhibits septic shock) at times zero and then again at 21 days. Blood can be obtained from the central ear artery at intervals to monitor development antibodies. The rabbits can be humanely sacrificed with an overdose of pentobarbital.

EXAMPLE 7

Treatment of an Inflammatory Response

The present invention features method of reducing or preventing an inflammatory response such as inflammatory bowel disease or rheumatoid arthritis in a mammal (e.g., a human). In general these methods involve administration of a compound (e.g., hemopexin (or a protein containing a hemopexin polypeptide), vanin-3, transthyretin, alpha-fetoprotein, or dermcidin) in an amount sufficient to reduce or prevent the inflammatory response. Administration of the compound(s) may decrease a cytokine response in the mammal, including a decrease in TNFα, IL-6, or IL-8 expression or activity. Alternatively administration of the compound(s) may increase a cytokine response, including an increase in IL-10 expression or activity. Inflammatory responses that may be treated by administration of the compounds include, for example, those involving p38 MAP kinase, erk1/2, and NF-κB activation. In particular, administration of the compound(s) may be used in cases where the inflammatory response results in sepsis caused by a bacterial toxin such as a component of a gram-negative bacterium (e.g., LPS).

The compound is typically administered to the subject by means of injection using any routes of administration such as by intrathecal, subcutaneous, submucosal, or intracavitary injection as well as for intravenous or intraarterial injection. Thus, the compound may be injected systemically, for example, by the intravenous injection of the compound into the patient's bloodstream or alternatively, the compound can be directly injected at the site of an inflammation.

The compound(s) may be administered to the subject in a single dose or in multiple doses. When multiple doses are administered, the doses may be separated from one another by, for example, one day, two days, one week, two weeks, or one month. For example, a compound that modulates a cytokine response may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound that modulates a cytokine response can be increased if the lower dose does not provide sufficient anti-inflammatory activity. Conversely, the dosage of a compound that modulates a cytokine response can be decreased if the inflammation is cleared from the patient.

While the attending physician ultimately will decide the appropriate amount and dosage regimen, a therapeutically effective amount of a compound that modulates a cytokine response, may be, for example, in the range of about 0.0035 μg to 20 μg/kg body weight/day or 0.010 μg to 140 μg/kg body weight/week. Desirably a therapeutically effective amount is in the range of about 0.025 μg to 10 μg/kg, for example, about 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 μg/kg body weight administered daily, every other day, or twice a week. In addition, a therapeutically effective amount may be in the range of about 0.05, 0.7, 0.15, 0.2, 1.0, 2.0, 3.0, 4.0, 5.0, 6.0, 7.0, 8.0, 10.0, 12.0, 14.0, 16.0, or 18.0 μg/kg body weight administered weekly, every other week, or once a month. Furthermore, a therapeutically effective amount of a compound that modulates a cytokine response may be, for example in the range of about 100 μg/m$^2$ to 100,000 μg/m$^2$ administered every other day, once weekly, or every other week. In a desirable embodiment, the therapeutically effective amount is in the range of about 1000 μg/m$^2$ to 20,000 μg/m$^2$, for example, about 1000, 1500, 4000, or 14,000 μg/m$^2$ of a compound that modulates a cytokine response administered daily, every other day, twice weekly, weekly, or every other week.

The administration of a compound that modulates a cytokine response may be by any suitable means that results in a concentration of the compound that modulates a cytokine response that, combined with other components, has anti-inflammatory properties upon reaching the target region. The compound may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions containing hemopexin (or a protein containing a hemopexin polypeptide), vanin-3, transthyretin, alpha-fetoprotein, or dermcidin as the active compound may be formulated to release the active compound immediately upon administration or at any predetermined time or time period after administration. The latter types of compositions are generally known as controlled release formulations. A pharmaceutical composition may be in a form suitable for sterile injection. To prepare such a composition, the suitable compound that modulates a cytokine response is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

All patents, patent applications, and publications mentioned in this specification are herein incorporated by reference to the same extent as if each independent patent, patent application, or publication was specifically and individually indicated to be incorporated by reference.

What is claimed is:

1. A method of reducing an inflammatory response or reducing the risk of developing an inflammatory response resulting from a bacterial or viral infection or the presence of a bacterial toxin in a mammal, said method comprising administering to said mammal human hemopexin or an amino acid sequence that is at least 95% identical to that of human hemopexin and comprises at least one hemopexin domain of human hemopexin, in an amount sufficient to reduce said inflammatory response or reduce the risk of developing said inflammatory response.

2. The method of claim 1, wherein said inflammatory response results from the presence of a bacterial toxin.

3. The method of claim 2, wherein said bacterial toxin is a component of a gram-negative bacterium.

4. The method of claim 3, wherein said bacterial toxin is lipopolysaccharide.

5. The method of claim 1, wherein said administering decreases a cytokine response.

6. The method of claim 5, wherein said cytokine response comprises a decrease in Tumor Necrosis Factor $\alpha$, IL-1, IL-6, or IL-8 expression or activity.

7. The method of claim 1, wherein said inflammatory response comprises p38 MAP kinase, erk1/2, or NF-$\kappa$B activation.

8. The method of claim 1, wherein said mammal is a human.

9. The method of claim 1, wherein said administering comprises administering human hemopexin.

10. The method of claim 1, wherein said administering comprises administering an amino acid sequence that is at least 95% identical to the amino acid sequence of human hemopexin and comprises at least one hemopexin domain of human hemopexin.

11. The method of claim 10, wherein said amino acid sequence is at least 99% identical to the amino acid sequence of human hemopexin and comprises at least one hemopexin domain of human hemopexin.

* * * * *

UNITED STATES PATENT AND TRADEMARK OFFICE
CERTIFICATE OF CORRECTION

| | | |
|---|---|---|
| PATENT NO. | : 8,821,851 B2 | Page 1 of 1 |
| APPLICATION NO. | : 12/225496 | |
| DATED | : September 2, 2014 | |
| INVENTOR(S) | : Warren et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1276 days.

Signed and Sealed this
Fifteenth Day of September, 2015

Michelle K. Lee
*Director of the United States Patent and Trademark Office*